United States Patent [19]
Ellegood et al.

[11] Patent Number: 6,137,860
[45] Date of Patent: Oct. 24, 2000

[54] DIGITAL RADIOGRAPHIC WELD INSPECTION SYSTEM

[75] Inventors: John P. Ellegood, Englewood; Blaine J. Wiltshire, Littleton, both of Colo.; Marion D. Barker, Sunnyvale; Lee M. Klynn, Los Altos, both of Calif.

[73] Assignee: Lockheed Martin Corporation, Bethesda, Md.

[21] Appl. No.: 09/376,706

[22] Filed: Aug. 17, 1999

Related U.S. Application Data

[60] Provisional application No. 60/096,848, Aug. 18, 1998.

[51] Int. Cl.$^7$ .................................................. G01N 23/02
[52] U.S. Cl. ................................ 378/58; 378/59; 378/62; 228/104; 73/865.8
[58] Field of Search ................................. 378/51, 58, 59, 378/62; 228/104; 73/865.8

[56] References Cited

U.S. PATENT DOCUMENTS

| | | | |
|---|---|---|---|
| 4,490,833 | 12/1984 | Inomata et al. | 378/58 |
| 4,680,470 | 7/1987 | Heald | 378/58 |
| 4,694,479 | 9/1987 | Bacskai et al. | 378/58 |
| 4,924,481 | 5/1990 | Vaughn | 378/59 |
| 5,182,775 | 1/1993 | Matsui et al. | 382/8 |
| 5,187,728 | 2/1993 | Vaughn | 378/59 |
| 5,439,157 | 8/1995 | Geier et al. | 228/9 |
| 5,524,038 | 6/1996 | Fong | 378/4 |
| 5,594,253 | 1/1997 | Bueno et al. | 250/486.1 |
| 5,636,299 | 6/1997 | Bueno et al. | 385/15 |
| 5,648,619 | 7/1997 | Gustafsson et al. | 73/865.8 |

*Primary Examiner*—David V. Bruce
*Assistant Examiner*—Drew A. Dunn
*Attorney, Agent, or Firm*—Marsh Fischmann & Breyfogle, LLP

[57] ABSTRACT

Disclosed is a weld inspection system that utilizes an automated digital radiographic camera and control system to generate and review digital X-ray images of the weld seam. The weld inspection system is mountable onto the weld fixture, such that the weld inspection system can inspect welds upon completion of welding operations while the barrel panels are still clamped in the weld fixture. The digital radiographic camera includes a fiber optic scintillator x-ray to light conversion screen coupled to a high resolution charged coupled device (CCD) camera to produce digital radiographic images of a portion of the weld between welded barrel panels. An X-ray source is located in a shielded housing which is attached to a carriage that is movably mounted to the vertical weld fixture on the convex side of the barrel weld. The digital radiographic camera is attached to a carriage that is movably mounted to the vertical weld fixture on the concave side of the barrel weld.

24 Claims, 8 Drawing Sheets

DIGITAL RADIOGRAPHIC WELD INSPECTION SYSTEM

RELATED APPLICATION

This application claims the benefit of U.S. Provisional Application No. 60/096,848, filed on Aug. 18, 1998.

FIELD OF THE INVENTION

This invention relates to weld inspection systems, and more particularly, to an automated digital radiographic camera and control system for use in a weld inspection system.

BACKGROUND OF THE INVENTION

Aluminum barrels (e.g., cylinders) are weldable to domes (e.g., hemispheres) to make launch vehicle propulsion or fuel tanks. Such barrels may be made from four 90° curved panels or five 72° curved panels that are weldable together along longitudinally extending seams in a vertical weld fixture or tool. Generally, for purposes of welding the panels to form a fuel tank, the panels may be placed on a horizontal turntable of the vertical weld fixture and then rotated about a vertical axis into clamping fingers of the vertical weld fixture. Thereafter, a one or two torch-single pass/variable polarity gas tungsten arc (VPGTA) system may be used to fusion-weld butt jointed panels together. For a four panel fuel tank, this process is repeated four times to produce a complete barrel, and five times for a five panel fuel tank.

After welding, the barrel is removed from the vertical weld fixture and transported to a weld inspection area. This is a very cumbersome and labor intensive process due to the size and weight of the completed barrel. It may take several riggers several hours to transport the barrel. The quality requirements for the weld joints are very high due to the high pressures and variable temperatures to which launch vehicle propulsion tanks and fuel tanks are exposed. Types of undesirable defects that may be encountered in the welds during inspection may include porosity, cracks, oxide inclusions, burn through holes, and lack of fusion. Factors which can contribute to such defects include the temperature, humidity, and barometric pressure at the time the weld is performed, along with oxidation, alloy variations, and imperfections of the weld wire itself.

There are several well known weld inspection methods for revealing possible weld defects. One basic method is X-ray photographing. Typically, in X-ray photography, X-ray film is placed on one side of the weld seam and an X-ray source is placed on the other side. The X-ray film is then exposed by the X-ray source through a portion of the weld. The X-ray source and a new X-ray film are then moved to a next position along the weld seam, and the next portion of X-ray film is exposed. This process is repeated until 100% of the entire length of the weld seam has been X-ray photographed. The X-ray film is then developed and reviewed by an inspector. Any defects found by the inspector are noted, located, and marked on the weld seams. The barrel is then repositioned in the vertical weld fixture and the marked areas are rewelded. The barrel is once again removed from the vertical weld fixture, placed in the weld inspection area, and the rewelded portions of the weld seam are X-rayed again. Upon developing and reviewing the X-ray film, if the defects have not been corrected, the barrel is returned once more to the vertical weld fixture for further rewelding. This process is very time consuming and labor intensive.

When thicker barrel material is used, due to penetration limitations of current film-based X-ray devices and the difficulty of detecting defects in aluminum, multiple films may be required to image the full range of thickness for each portion of the weld to adequately inspect the weld. In such cases, for each section of the weld, a first X-ray film is exposed for the first part of the thickness of the weld, and a second X-ray film is exposed for a next part of the thickness of the weld, and so on. This limitation significantly increases the time it takes to inspect variable thickness weld seams.

SUMMARY OF THE INVENTION

It is an object of the present invention to inspect a weld seam while two barrel panels joined by the weld are still positioned within a weld fixture or tool.

Yet another object of the invention is to inspect a weld seam immediately after the completion of welding operations while the two barrel panels joined by the weld are still clamped in the position where they were welded.

Still another object of the invention is to eliminate the use of film and the associated, time consuming developing process in obtaining images of a weld seam for weld inspection purposes.

A still further object of the invention is to reduce the recurrence of weld defects and repair welds through inspecting a weld seam and making adjustments to the parameters of a welding device before a next weld is performed.

Another object of the invention is to reduce the overall build cycle-time of a barrel by reducing the time required to perform a weld inspection.

Another object of the invention is to view images of the weld seam immediately after acquisition of the image.

Another object of the invention is to reduce the time required to inspect weld seams, including variable thickness weld seams.

Another object of the invention is to quickly generate an additional image of a portion of a weld seam from a slightly different position if the first image indicates some question as to the presence of any defects.

Another object of the invention is to reduce costs by eliminating the need to move the barrel to a weld inspection location, and to eliminate the need for X-ray film, X-ray film process chemicals, and X-ray film storage costs.

The above and other aspects of the invention are accomplished in a weld inspection system that utilizes a digital radiographic camera and position control system to generate and review digital images of the weld seam. The weld inspection system is mountable onto the weld fixture, such that the weld inspection system can inspect welds upon completion of welding operations.

In one aspect of the present invention, the digital radiographic camera consists of a fiber optic scintillator (FOS) x-ray to light conversion screen coupled to a high resolution charged coupled device (CCD) camera to produce digital radiographic images of a portion of the weld between welded panels of the barrel (e.g., first and second barrel panels). Each individual digital radiographic image generated is referred to as an tile image or tile. This non-film system allows tile images of the weld to be viewed within one minute upon acquisition on a display device, such as a CRT monitor, and eliminates development of film, which results in simplified image review, storage, and retrieval of digital radiographic records. As such, the system provides near real-time image acquisition with electronic image enhancements not available with conventional film techniques. Image acquisition time is on the order of 30 to 60 seconds, as compared to 15 to 20 minutes for film. Thus, one operator can inspect one entire weld seam in about one hour, compared to the conventional film technique which takes two men about one and a half hours each, for a total of three man-hours, to inspect a weld seam.

Moreover, the barrel welds can be radiographically inspected immediately upon completion of the weld while the barrel panels (e.g., first and second barrel panels) are still clamped in the weld fixture (e.g., full length weld inspection results within 75 minutes of weld completion). This allows improvements in the weld process, with attendant reduction of weld defects and weld repairs since each weld (e.g., weld connecting first and second barrel panels) may be inspected prior to proceeding with the next weld (e.g., weld connecting second and third barrel panels). Accordingly, weld parameters may be adjusted prior to starting another weld, thereby eliminating recurring weld problems. Additional benefits include reduced build cycle-time for assembling a launch vehicle propulsion or fuel tank and reduced labor costs associated with moving a barrel to a weld inspection area and then re-installing the barrel back in the weld fixture for a full length weld repair if required.

In one embodiment, an X-ray source is attached to a carriage that is movably mounted to the vertical weld fixture on the convex side of the barrel weld. The digital radiographic camera is attached to a carriage that is movably mounted to the vertical weld fixture on the concave side of the barrel weld. Both of these carriages are mounted below the weld torch carriages. After welding is complete, the weld carriages are parked out of the way at the top of the weld fixture, allowing weld inspection to be performed unhindered.

DETAILED DESCRIPTION

Figure 1:
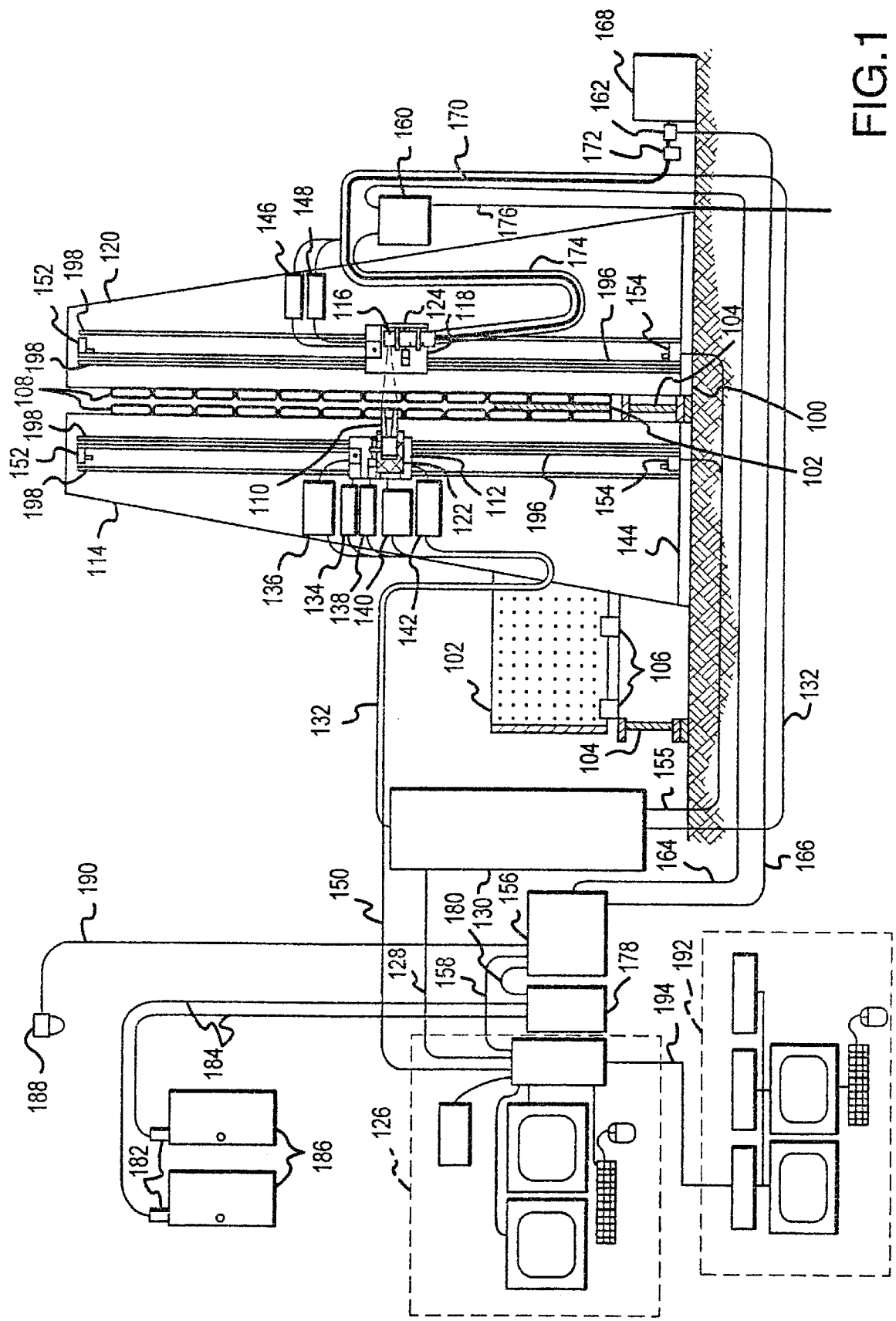
FIG. 1 shows a schematic/block diagram of the weld inspection system of the present invention.

FIG. 1 shows a schematic/block diagram of the weld inspection system of the present invention. Referring now to FIG. 1, vertical weld fixture 100 is used to assemble aluminum barrels (e.g., cylinders) from four 90° curved panels, or five 72° curved panels, that are welded together along longitudinally extending seams to make cylinders. These cylinders are then welded to domes (e.g., hemispheres) to make launch vehicle propulsion or fuel tanks.

Generally, for purposes of welding curved panels to form a fuel tank cylinder, the barrel panels 102 (shown partially cutaway) may be placed on turntable 104 (shown partially cutaway) of vertical weld fixture 100, resting on grips 106, and then rotated into clamping fingers 108 of vertical weld fixture 100. Thereafter, a two torch-single pass/VPGTA system (not shown in FIG. 1) or other appropriate welding system may be used to fusion-weld barrel panels 102 together. For a four panel fuel tank, this process is repeated four times to produce a complete barrel, and five times for a five panel fuel tank, or N times for an N panel cylinder.

As noted hereinabove, the weld fixture has a vertical axis. Of importance, the weld inspection system of the present invention is mounted onto vertical weld fixture 100, such that the weld inspection system can inspect welds upon completion of fusion-welding operations. Digital radiographic camera 110 (more fully described in FIG. 2) is mounted to camera carriage 112, which is movably mounted on inside column 114 via rails 198. X-ray source 116 is mounted to X-ray carriage 118, which is movable mounted on outside column 120 via rails 198. Both camera carriage 112 and X-ray carriage 118 have bearings (not shown in FIG. 1) riding against rails 198, and a rack-and-pinon type gear (also not shown in FIG. 1) along one rail. Additionally, digital radiographic camera 110 is movably mounted to sub-slide 122 within camera carriage 112, allowing movement in-and-out, or radially horizontally and perpendicular to the longitudinal weld seam. Also, X-ray source 116 is movably mounted to sub-slide 124 within X-ray carriage 118, allowing movement side-to-side, or tangentially, in relation to the barrel panels at the weld seam. The radial movements of digital radiographic camera 110 and the tangential movements of X-ray source 116 have in and out switches (not shown in FIG. 1) establishing in and out limits, and initialization switches (also not shown in FIG. 1) establishing initialization positions. Inside column 114, outside column 120, and turntable 104 are mounted to base platform 144 of vertical weld fixture 100. Camera carriage 112 and X-ray carriage 118 are each positioned below a weld torch carriage (not shown in FIG. 1) on inside column 114 and outside column 120.

X-ray source 116 bombards with X-rays a portion of the weld between welded barrel panels 102 (e.g., first and second barrel panels) held by clamping fingers 108 in vertical weld fixture 100. The X-rays that pass through the weld and strike the input sensor of digital radiographic camera 110 produce radiographic images of that portion of the weld. Due to the physical restraints of vertical weld fixture 100, X-ray source 116 typically operates at 60 kV and 10 mA to give proper exposure to digital radiographic camera 110.

This non-film system allows images of the weld to be viewed within one minute of acquisition on a display device (e.g., CRT monitor) and eliminates development of film, which results in an efficient, simplified image review, storage, and retrieval of digital radiographic records. As such, the system provides nearly real-time image acquisition and electronic image enhancements not available with conventional film techniques. Moreover, the welds can be radiographically inspected immediately upon completion of the weld while the barrel panels 102 (e.g., first and second barrel panels) are still clamped in vertical weld fixture 100 (e.g., full length weld inspection results within 75 minutes of weld completion) This allows improvements in the weld process, with attendant reduction of weld defects and weld repairs since each weld (e.g., weld connecting first and second barrel panels) may be inspected prior to proceeding with the next weld (e.g., weld connecting second and third barrel panels). Accordingly, weld parameters may be adjusted prior to starting another weld, thereby eliminating recurring weld problems. Additional benefits include reduced build cycle-time and cost elimination for assembling a launch vehicle fuel tank and reduced labor costs associated with re-installing a barrel into vertical weld fixture 100 for a full length weld repair if required.

Figure 2:
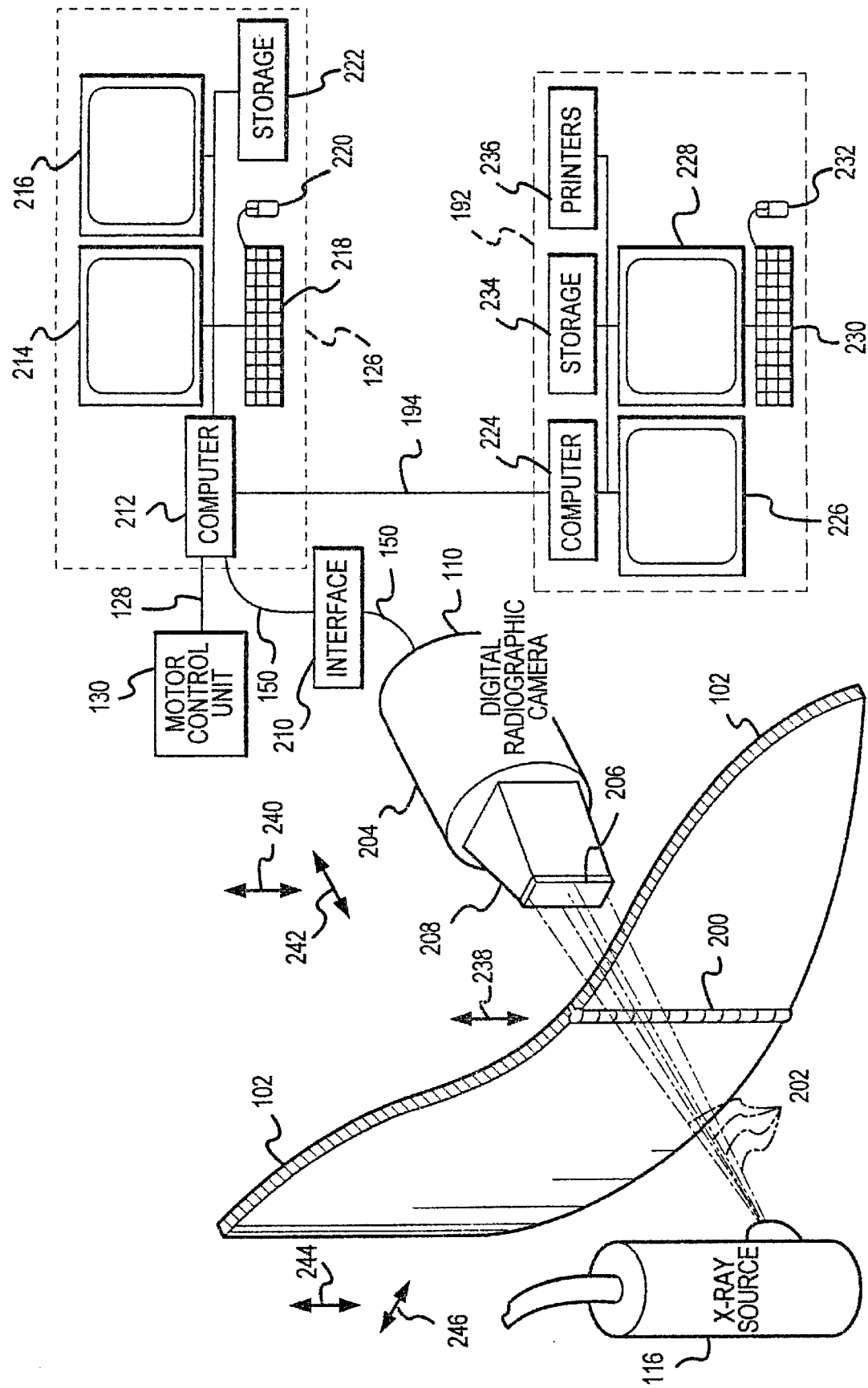
FIG. 2 shows a schematic/block diagram of the data acquisition workstation and the image review workstation of the weld inspection system of the present invention.

The weld inspection process is controlled by data acquisition workstation 126, more fully described in FIG. 2. Data acquisition workstation 126 sends control signals over cable 128 to motor control unit 130, which in turn controls various motors, switches, and brakes through signals sent over circuits 132.

Inside vertical motor drive 134, which is a stepper motor, moves camera carriage 112 up-and-down inside column 114. The physical characteristics of vertical weld fixture 100 necessitate having a pair of collision avoidance sensors 136, one mounted directly above and one mounted directly below digital radiographic camera 110, which will stop the movement of camera carriage 112 if something is obstructing the path of travel, preventing damage to digital radiographic camera 110. Radial motor drive 138, which is a stepper motor, moves digital radiographic camera 110 in-and-out, or radially horizontally, on sub-slide 122 and perpendicular to the longitudinal weld seam. Camera cooler 140 assists in cooling the charged coupled device (CCD) within digital radiographic camera 110 in order to reduce electronic noise. The CCD also has a thermoelectric cooler internal to the CCD camera head (not shown in FIG. 1). Camera cooler 140 is a liquid cooler (ethylene glycol based) that removes excess heat from the CCD camera head to enable the internal thermoelectric cooler to work more efficiently. A cooled CCD has lower dark current.

Camera electronics unit 142 reads out information from digital radiographic camera 110 and sends it to data acquisition workstation 126 over circuit 150. Signals from camera electronics unit 142 also coordinate the opening and closing of a shutter provided on the shielded housing (not shown in FIG. 1) of X-ray source 116. X-ray source 116 stays on for the entire weld inspection process. A shutter controller (also not shown in FIG. 1) receives the signals from camera electronics unit 142 and coordinates the X-ray flux with digital radiographic camera 110 exposure. The CCD is a full frame CCD. This means that the exposure must be halted in order to read out the CCD. Once the shutter is closed the exposed CCD can be read out.

Outside vertical motor drive 146, which is a stepper motor, moves X-ray carriage 118 up-and-down outside column 120. Tangential motor drive 148, which is a stepper motor, moves X-ray source 116 side-to-side, or tangentially, on sub-slide 124. Inside vertical motor drive 134 and outside vertical motor drive 146 each have a motor encoder (not shown in FIG. 1), which is a mechanism that tells exactly where camera carriage 112 and X-ray carriage 118 are in a vertical sense on inside column 114 or on outside column 120. These encoders generate pulses proportional to the distance moved to compute the vertical position location of camera carriage 112 and X-ray carriage 118. The encoders are not used to control position because they are not accurate enough. For example, the vertical encoders have a resolution of 1,273 counts per inch as opposed to 227,363 counts per inch for the stepper motor. The encoder position is compared to where the digital radiographic camera and X-ray source carriages should be based on the number of stepper pulses sent. So long as the encoder is within a pre-set tolerance of that expected position, no error is indicated. If the encoder is outside of the tolerance, the operator is warned and told to re-initialize that axis.

Inside vertical motor drive 134 and outside vertical motor drive 146 each have a brake on the pinion shaft of the rack and pinion mechanism (not shown in FIG. 1) for holding vertical movement.

Top end-of-travel switches 152 and bottom end-of-travel switches 154 send signals over circuits 196 and circuit 155 whenever camera carriage 112 or X-ray carriage 118 reach the top or bottom of inside column 114 or outside column 120. When the switches open, the current is cut to the drive motors to rapidly halt motion in that direction. When one of these switches is open, the direction of travel for that motor is enabled only in the direction towards the other switch.

The top park switches and bottom park switches are used to ensure camera carriage 112 or X-ray carriage 118 are properly parked. They are placed in the bottom park position to be out of the way of the welding heads during weldment and the panels during panel insertion, and in the top park position to be out of the way during routing of the weld seam. The motors and encoders all use relative position information. Therefore, to initialization locations after the system is powered on, there is an initialization switch for each axis. The two vertical axes have the initialization switches located a few inches above the bottom park switches. The two horizontal axes do not have park locations. They each have two end-of-travel switches and one initialization switch (not shown in FIG. 1).

Top end-of-travel switches 152 and bottom end-of-travel switches 154 send signals over circuits 196 and circuit 155 whenever camera carriage 112 or X-ray carriage 118 reach the top or bottom of inside column 114 or outside column 120. When the switches open, the current is cut to the drive motors. When it is time to proceed in the opposite direction, the switches close, and the current is restored causing camera carriage 112 or X-ray carriage 118 to move away from the switch. A home position is established for camera carriage 112 and X-ray carriage 118 when each activate bottom end-of-travel switches 154. Top and bottom park switches (not shown in FIG. 1) establish a top and bottom park position for camera carriage 112 and X-ray carriage 118, and initialization switches (not shown in FIG. 1) establishes an initialization position for camera carriage 112 and X-ray carriage 118. When first powered on, camera carriage 112 and X-ray carriage 118 go down until the bottom park switches are tripped, then go up until the initialization switches are tripped. A precise location with respect to the initialization switch is established. The location of the top and bottom park position with respect to the initialization location is measured initially and stored in a parameter file.

Data acquisition workstation 126 also sends control signals to X-ray source controller 156 over circuit 158. X-ray source controller 156 controls X-ray high voltage generator 160 by sensing the X-ray coolant flow switch 162 through X-ray control cable 164 and X-ray coolant flow switch cable 166. X-ray coolant flow switch 162 senses flow of coolant in coolant chiller 168 to insure coolant is circulating through X-ray source 116 and through hose 170 and is monitored by flow rate indicator 172. High voltage current is delivered over cable 174 to X-ray source 116. X-ray high voltage generator 160 is grounded through earth ground 176.

Safety features required by stringent state guidelines and the physical characteristics of vertical weld fixture 100 include X-ray interlock panel 178 connected to X-ray source controller 156 through circuit 180. Door switches 182 send signals through circuits 184 if doors 186 are opened while X-ray source 116 is operational, cutting the power. Doors 186 lead into areas in and around vertical weld fixture 100 that are not safe for people to be in when X-rays are being generated. X-ray on lamp 188 turns on via circuit 190 when X-rays are being generated. In addition, a bell (not shown in FIG. 1) sounds at the start of X-ray generation.

Image review workstation 192, more fully described in FIG. 2, accesses the digital images generated by digital radiographic camera 110 that are stored on disk by the data acquisition workstation 126. Disks on both the data acquisition workstation 126 and the review workstation 192 are available over high-speed Ethernet through cable 194.

FIG. 2 shows a schematic/block diagram of the data acquisition workstation and the image review workstation of the weld inspection system of the present invention. Referring now to FIG. 2, barrel panels 102 (shown partially cutaway) are joined together by weld 200, and are held in place in vertical weld fixture 100 (FIG. 1). X-ray source 116 bombards a portion of weld 200 with X-rays 202, which are absorbed in digital radiographic camera 110 after passing through that portion of weld 200. Due to the physical constraints of vertical weld fixture 100, the distance between X-ray source 116 and weld 200 is approximately 18.0 inches. The distance between X-ray source 116 and digital radiographic camera 110 is approximately 19.5 inches.

X-ray generation in one embodiment of the invention is accomplished with a constant potential system, where X-ray source 116 is a Philips MCN 165 tube head (3.0 mm and 0.4 mm focal spots) or a Comet MXR-160 tube head (two 0.4 mm focal spots). X-ray high voltage generator 160 is a Gulmay FL100 dual focus, 640 watt generator. X-ray source controller 156 is a Gulmay MP-1 Controller, and coolant chiller 168 is a Bernard water cooler. A shielded tube enclosure with a pneumatic shutter (not shown in FIG. 2) houses the x-ray tube. The lead enclosure is designed to provide radiation protection sufficient at one foot in any direction (except in primary beam) to be considered an Unrestricted Area (per Colorado Department of Health, Rules and Regulations Pertaining to Radiation Control, 6 CCR 1007).

The shutter opens and closes in approximately 0.2 seconds. A Victoreen Model 1060 Area Monitor, using a Model 90-12 Energy Compensated Geiger Muller probe (not shown in FIG. 2), is used to verify when X-rays are emitted from the lead enclosure. The Geiger Muller probe is located near digital radiographic camera 110. For the best results, a collimator (not shown in FIG. 2) is used to limit the X-ray flux illumination to the active field of view of digital radiographic camera 110. The X-rays emanate in an expanding cone pattern from X-ray source 116. The collimator is typically a rectangular cutout in a circular piece of lead. The collimator minimizes X-ray scatter impinging on the camera system and provides increased radiation shielding. The presence of scattered X-rays can cause a decrease in image sensitivity and raise safety concerns.

Digital radiographic camera 110 is a state of the art Charge Coupled Device (CCD) camera 204 mated to a fiber optic scintillator X-ray to light converter (not shown in FIG. 2) located behind light tight shield 206. Examples of fiber optic scintillator X-ray to light converters are disclosed in U.S. Pat. Nos. 5,636,299 and 5,594,253 by Bueno et. al, and U.S. Pat. Nos. 5,108,959, 5,122,671 and 5,391,320 by Buchanan et. al, all of which are incorporated specifically by reference herein in their entirety. In the current application, a mirror coating of aluminum was placed on the x-ray source side of the fiber optic scintillator. The weld inspection system of the present invention follows the standard operating procedures as outlined in ASTM E1255-96, Standard Practice for Radioscopy, and ASTM E1411-95, Standard Practice for Qualification of Radioscopic Systems.

CCD camera 204 consists of a fiber optic camera head (not shown in FIG. 2), camera cooler 140 and camera electronics unit 142 (FIG. 1), and interface 210.

The fiber optic scintillator x-ray to light converter has a fixed rectangular field of view of approximately three inches by one inch. The one inch width was selected to match the one inch section of weld 200 visible within clamping fingers 108 (FIG. 1) of vertical weld fixture 100. The three inch height was selected in light of commercially available and affordable CCD chips and a desire to optimize inspection time while maintaining sufficient spatial resolution to image critical features within weld 200. X-rays 202 transmitted through weld 200 are absorbed in the fiber optic scintillator x-ray to light converter located behind light tight shield 206. In the fiber optic scintillator, each absorbed X-ray is converted into many light photons. A straight fiber optic conduit (not shown in FIG. 2) housed within extender 208 conducts light from the fiber optic scintillator x-ray to light converter to a tapered fiber optic bundle (also not shown in FIG. 2) within CCD camera 204. The purpose of extender 208 is to allow the fiber optic scintillator x-ray to light converter to be positioned close enough to weld 200 in light of the physical restraints of vertical weld fixture 100.

The fiber optic bundle de-magnifies the image and transmits the light to the CCD chip (also not shown in FIG. 2) within CCD camera 204, which is approximately 2,000 pixels square. Because of the input size of the fiber optic scintillator X-ray to light converter, only a region of approximately 2,000×660 pixels on the CCD chip are used. Each pixel in the CCD chip measures 0.0015 inch. The geometric unsharpness achieved in the invention is 0.0018 inch. X-ray image feature blurring can be measured by the total unsharpness which is a combination of geometric unsharpness and electron image unsharpness. At energies below 160 kV the electron range is very small.

In order to detect the smallest defects that require correction, based on program specific weld allowable criteria, the resolution of digital radiographic camera 110 is thirteen line pairs/mm as measured with a line pair gauge X-ray test pattern.

The readout rate for CCD camera 204 is 500 kpixels/second and the output of the CCD chip is digitized by a 12 bit analog-to-digital converter (ADC) (not shown in FIG. 2) so that maximum ADC amplitude (saturation) is a digital number (DN) of 4,095. Interface 210 converts the output from CCD camera 204 into a format usable by data acquisition workstation 126.

The charge wells within the CCD fill up linearly with electrons during illumination up to the saturation level or full well capacity for each pixel. The gain of the CCD electronics is matched to the full well capacity of the chip so that saturation occurs near the 4095 maximum ADC level. Unlike film, the response of the CCD chip is linear over a wide range of brightness levels so extremely wide latitude is possible. Under the standards of ASTM E1742, 2-2T penetrameter sensitivity is required to control radiographic image quality. Two percent penetrameter sensitivity has been demonstrated on ¼' and 3' thick aluminum in the same image. In most cases it is desirable to get the brightness level in the area of interest as high as practical. Typically, a mean or average level of 2500 to 3500 DN is used as derived from empirical study.

The fiber optic conduit and tapered fiber optic bundle exhibit a pattern of fixed noise as the result of variations in light transmissions of individual fibers or groups of fibers. To eliminate this condition, a procedure known as "normalization" is used.

Normalization uses a dark, or offset, image and a blank image to adjust all pixels to have uniform gains and no offset in X-ray sensitivity. The dark image is acquired without X-ray illumination. The CCD is cleared, charges are built up for the same length of time as the blank exposure, and then the CCD is read out and displayed, yielding the dark image. The two images, dark and blank, are used to normalize each subsequent image for offset and gain. This provides a pixel by pixel normalization so each pixel then has the same effective gain.

The blank image is acquired through a defect free uniform piece of the same material type and thickness as will be inspected using the same X-ray parameters as the final weld inspection. Both images are generally acquired with the same acquisition time as the final weld inspection.

Weld 200 has a longitudinal axis represented by double arrow 238. Camera carriage 112 (FIG. 1) containing digital radiographic camera 110 is moved up-and-down inside column 114 (FIG. 1) along an axis represented by double arrow 240, which is parallel to axis 238. In addition, radiographic camera 110 is moved in-and-out, or horizontally, within sub-slide 122 (FIG. 1), along an axis represented by double arrow 242, which is perpendicular to axis 238 and axis 240, and passes through axis 238 and 240.

X-ray carriage 118 (FIG. 1) containing X-ray source 116 is moved up-and-down outside column 120 (FIG. 1) along an axis represented by double arrow 244, which is parallel to axis 238 and axis 240. In addition, X-ray source 116 can be moved side-to-side, or tangentially, on sub-slide 124 (FIG. 1) along an axis represented by double arrow 246. Axis 246 is perpendicular to axes 238, 240, 242, and 244.

Each portion of weld 200 is X-rayed with X-ray source 116 and digital radiographic camera 110 aligned at multiple horizontal positions along the length of weld 200. The center of beam generation of X-ray source 116 and the center of the fiber optic scintillator of digital radiographic camera 110 are aligned horizontally to plus or minus 0.014 inch for each tile image produced. When camera carriage 112 and X-ray carriage 118 are in the home position, they are aligned with each other within this tolerance.

If, upon review, a given tile image indicates that there might be a defect in the weld that cannot be discerned for certain with the current tile image, a new tile image may be taken with slightly altered positions of X-ray source 116 or digital radiographic camera 110, or both. Camera carriage 112 and source carriage 118 are moved to the proper tile position. X-ray source 116 is then moved tangentially along sub-slide 124, or digital radiographic camera 110 is moved radially along sub-slide 122. Adjusting the positions of X-ray source 116 and digital radiographic camera 110 may yield a better tile image for discerning defects in the suspect portion of the weld.

Data acquisition workstation 126 consists of computer 212, display devices 214 and 216, keyboard 218, mouse 220, and external storage device 222. A single display device may also be used, but two display devices are preferred in order to provide the operator with superior tools. Imaging display and control software running on computer 212 controls the data acquisition process. To adequately support the imaging display and control software, computer 212 is typically a Sun Ultra 1 computer with four internal two GB hard disk drives, floppy drive, and a CD-ROM. External storage device 222 may be an 8 mm tape drive, CD drive, optical disk, or DVD drive. Information stored on disk in both the data acquisition workstation 126 and the review workstation 192 are available to either computer over high-speed Ethernet through cable 194. Cable 128 to motor control unit 130 connects to an RS232 port on computer 212. Mouse 220 is active over both display devices 214 and 216, behaving as if display devices 214 and 216 were one continuous screen. Display device 216 is typically a twenty inch color monitor and presents the graphic user interface to the operator, allowing the operator to exercise input and control over the system. Display device 214 is typically a twenty inch color monitor operating in black and white. Display device 214 displays images of tiles from digital radiographic camera 110 in large mode. After each tile image is displayed, the tile image is automatically given a filename and saved to a hard disk drive.

Image review workstation 192 consists of computer 224, display devices 226 and 228, keyboard 230, mouse 232, external storage device 234 and one or more printers 236. A single display device may also be used, but two display devices have proven to be superior. The same imaging display and control software used on the data acquisition computer 212 also runs on computer 224 where it is used to control the imaging review process. Computer 224 is typically a Sun Ultra 1 computer with four internal two GB hard disk drives, floppy drive, and a CD-ROM. External storage device 234 may be an 8 mm tape drive, CD drive, or DVD drive. Image review workstation 192 accesses the digital images stored on disk. Mouse 232 is active over both display devices 226 and 228, behaving as if display devices 226 and 228 were one continuous screen. Display device 228 is typically a twenty inch color monitor and presents the graphic user interface to the operator, allowing the operator to exercise input and control over the system. Display device 226 is typically a twenty inch color monitor operating in black and white. Display device 226 displays images of tiles received from computer 212 in large mode. Printers 236 are typically a laser printer for printing log files and quick views of tile images, and a dye sublimation image printer for printing high quality hard copies of images, such as 300×300 dots-per-inch resolution yielding photo realistic, continuous-tone images.

X-rays transmitted through a portion of weld 200 are absorbed in the fiber optic scintillator located behind light tight shield 206 at the front of digital radiographic camera 110. The light generated by the fiber optic scintillator is channeled by the fiber optic conduit and tapered fiber optic bundle, which then transmits the light to the low-light sensitive CCD chip.

Light photons release electrons at the CCD chip which are trapped in individual charge wells. The array of approximately 2000×2000 charge wells make up the pixels of CCD camera 204. Of these, an array of approximately 2000×660 are illuminated by the three inch by one inch fiber optic scintillator. The electrons are stored in the charge wells until CCD camera 204 is read out. As long as the charge wells don't overflow (saturate), the signal in each pixel will continue to build up linearly during X-ray exposure time to a maximum digital number of 4095. Depending upon the type and thickness of the material welded, exposure time may vary from a few seconds up to a minute. Typical exposure times are ten to thirty-five seconds.

Once the exposure is completed, CCD camera 204 is read out by camera electronics unit 142 (FIG. 1) which measures the number of electrons in each charge well. The CCD camera 204 is a full frame CCD. That means that the exposure must be halted in order to read it out. The shutter provided on the shielded housing accomplishes this purpose. A signal from camera electronics unit 142 to X-ray source controller 156 (FIG. 1) coordinates the X-ray flux with the exposure of CCD camera 204. A collimator (not shown in FIG. 2) is used to limit the x-ray flux illumination to the active field of view of CCD camera 204.

Images from digital radiographic camera 110 first appear on the display with the 2.75 inch imaged weld length from each tile spread across a 14 inch viewable screen area for an apparent optical magnification of about 5×. Because the screen displays an image width of 1024 pixels, this image shows only ¼ of the available pixels. A 2× digital zoom is used to show all pixels, within any portion of the image. The operator can scroll around at this zoom level or at higher zoom to achieve effective optical magnifications of 10× or higher.

Figure 3:
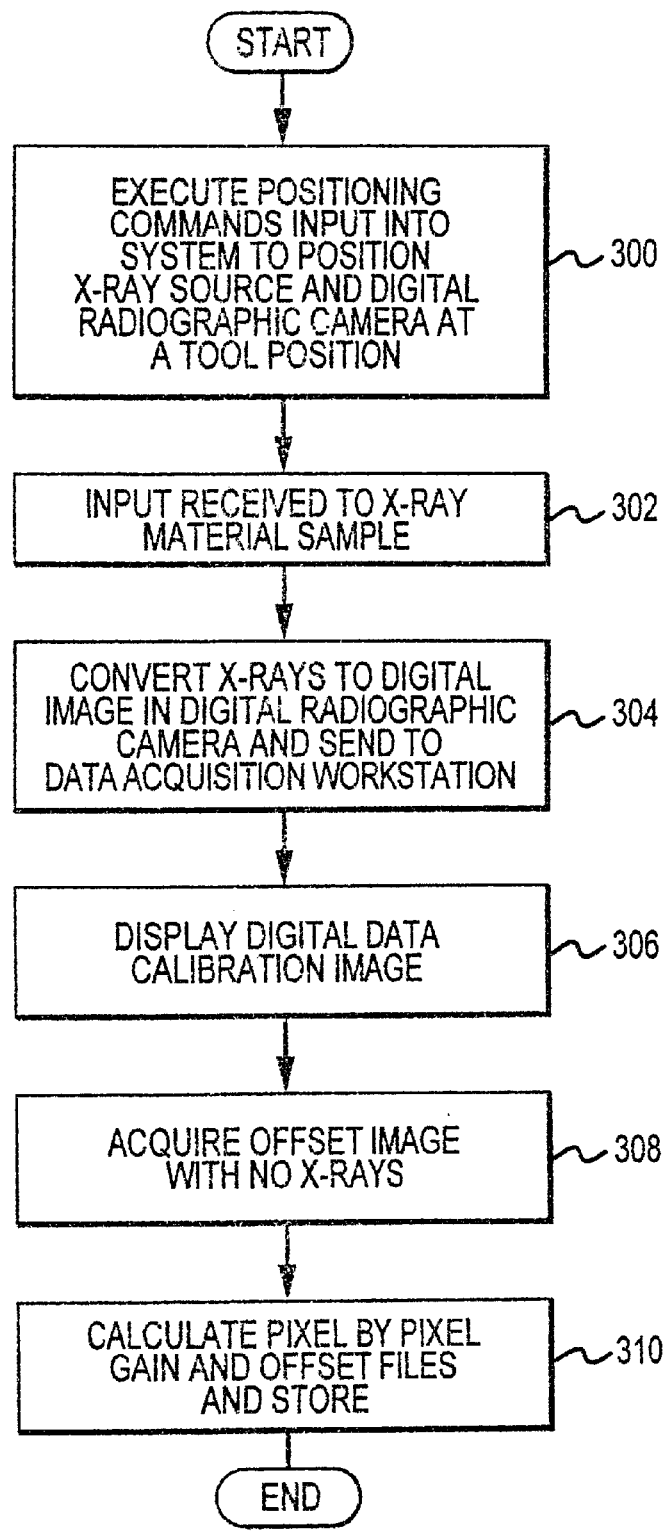
FIG. 3 shows a block diagram of generating an image normalization file used in the weld inspection system of the present invention.

FIG. 3 shows a block diagram of generating an image normalization file used in the weld inspection system of the present invention. In order to generate an image normalization file, a uniform material sample without defects, typically four inches long per side, is placed in a holding tool that properly positions the material sample between X-ray source 116 and digital radiographic camera 110 (FIG. 1). The holding tool is secured to vertical weld fixture 100 at a position below where barrel panels 102 rest on turntable 104 (FIG. 1). This position is referred to as the normalization position.

Referring now to FIG. 3, in step 300, positioning commands received from an operator working at data acquisition workstation 126 running the imaging display and control software are executed. Executing the positioning commands causes digital radiographic camera 110 and X-ray source 116 to be moved respectively to the normalization positions along inside column 114 and outside column 120 (FIG. 1). The normalization position is a predetermined distance away from each respective home position of camera carriage 112 and X-ray carriage 118. In step 302, input is received from the operator to bombard the material sample with X-rays from X-ray source 116 for a predetermined exposure time based on the type and thickness of the sample material. In step 304 the X-rays passing through the material sample are absorbed in digital radiographic camera 110, converted to light, and directed to the CCD chip as described above in FIG. 2. Camera electronics unit 142 reads out the image normalization set from the CCD chip and sends it through interface 210 (FIG. 2) to computer 212 in data acquisition workstation 126.

In step 306 the image normalization set is displayed on display devices 214 and 216, and is called a blank image. In step 308 an offset image, or dark image is acquired without X-ray illumination. In step 310 the offset image and blank images are used to calculate pixel by pixel the offset and gain, which are stored in an image normalizatin file, and the process of FIG. 3 ends.

After the normalization file is complete, the next operation is to select the sequence required to inspect the current barrel panel weld. However, all weld inspection sequences use an underlying PLUT. If this PLUT does not yet exist, then the operator must obtain one.

The manipulation control of X-ray source 116 and digital radiographic camera 110 is critical to automated acquisition of images along weld 200. X-ray source 116 and digital radiographic camera 110 must maintain the location of the normal from source to screen at the screen to an accuracy of ±14 mils (0.35 mm). However, the alignment between X-ray source 116 and digital radiographic camera 110 varies by more than this when traveling up the two independent rack and pinion tracks along inside column 114 and outside column 120. A PLUT is utilized that records the required vertical positions for X-ray source 116 and digital radiographic camera 110 for each nominal location, and allows for tangential and/or vertical motion of the source to compensate for angular misalignments.

Figure 4:
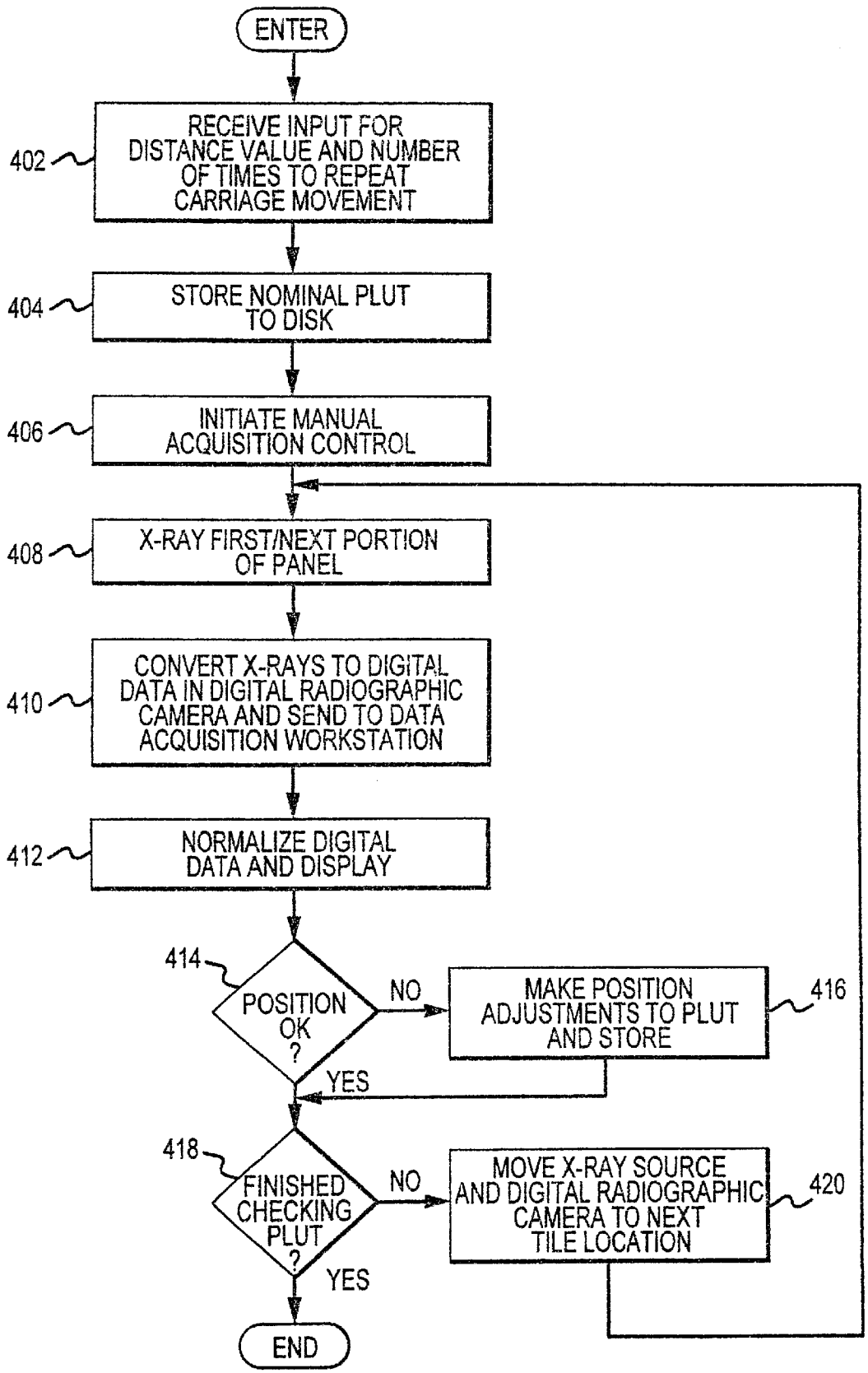
FIG. 4 shows a block diagram of generating a position look up table (PLUT) used in the weld inspection system of the present invention.

A software tool, whose use is described in FIG. 4, is included in the control software to make PLUT generation easier. Furthermore, it was assumed, and found to be true during testing, that the changes from a linear step required to keep the source and camera aligned from bottom to top of the barrel panel vary gradually along the length of weld 200. The software was configured to enable a separate PLUT to be used for each panel, but this was found to be unnecessary because the same PLUT worked for each panel inserted into the vertical weld assembly. In addition, the PLUT could be generated by using the software process described in FIG. 4 at every tenth or twentieth tile position and then using a smoothed line to estimate the required changes to the source vertical and tangential position at the intervening tiles. Because the PLUT is a simple text file of manipulator positions for each tile, these interpolations can be made offline with a spreadsheet and then imported into the motion control system for final verification.

FIG. 4 shows a block diagram of generating a PLUT used in the weld inspection system of the present invention. Referring now to FIG. 4, a full-length panel is inserted into vertical weld fixture 100 in such a way that the uniform panel (no weld portion) is viewed by the camera. In step 402, input is received from the operator for the parameters needed to generate a PLUT. The field of view of digital radiographic camera 110 is three inches vertically with a geometric magnification of about 1.083. Therefore the effective weld length imaged with each tile image is 2.77 inches. To obtain tile images with some overlap, vertical steps of 2.5 inches are used between tile images. The PLUT is generated in step 402 when the operator indicates Vertical Location for Bottom Edge of First Tile, Vertical Location for Top Edge of Last Tile, Vertical Center to Center Tile Spacing, Radial Camera Location, and Tangent Source Location. This will generate a PLUT with nominal values, which is automatically stored to disk in step 404 and becomes the current PLUT in use. Once accepted, a PLUT fine adjustment window is available to the operator to be used in conjunction with the manual acquisition control window.

In step 406, the operator initiates the manual acquisition control window. The operator manually adjusts the X-ray source kV and mA to the desired value and enters the image exposure time in the manual acquisition control window. Typically, the selected exposure time can be quite short, e.g. 5 seconds, since the feature used to verify alignment doesn't need long exposures to be apparent. In steps 408 through 412, the operator commands the manipulators to go to the selected tile location, exposes and acquires digital data, and displays a normalized image.

In step 414, the operator determines if the alignment of X-ray source 116 and digital radiographic camera 110 are within required tolerance from viewing the displayed normalized image in step 412. If the X-ray source 116 and digital radiographic camera 110 are not aligned within a tolerance of +/−0.014 inches, a characteristic artifact will be apparent in the normalized image of the uniform panel. This artifact arises from the fact that the fiber optic scintillator of digital radiographic camera 110 has a decrease in light generated in the region where the X-rays are exactly aligned with the fiber direction, i.e., at the source-to-detector normal. If the location of that normal changes, then the normalized image will exhibit a black and white indication. The black indication is the location of the new image normal and the white indication is the location of the image normal at the time the normalization files were acquired. This artifact is very faint and hard to discern in any image that is not almost completely uniform, which is why the PLUT adjustment must always be done with a uniform panel clamped in place of the normal welded structure.

If the operator determines in step 414 that an artifact is visible as displayed in step 412, then an adjustment to the PLUT is required. In step 416 the operator measures the center-to-center distance between the black and white indications. The vertical distance in pixels is used to adjust the source vertical position and the horizontal distance in pixels is used to adjust the source tangential position. The software automatically adjusts for geometric magnification and pixel size to generate the correction motion, which may be as small as 0.001 inches. Once this motion has been made, the PLUT is updated and saved to disk. Control then passes to step 418. If no artifact is seen in step 414 indicating that the position is not misaligned, then in step 418 the operator determines if he is finished examining the PLUT. If yes, the process ends. If more tile positions remain to be examined, then the operator in step 420 manually indicates the next tile to evaluate and X-ray source 116 and digital radiographic camera 110 are moved to the next tile location.

Once the full panel height has been investigated at a representative number of tiles, then the stored PLUT file is modified offline to interpolate the measured changes for the tiles that were not examined initially. The PLUT is then read in again and verified by acquiring a full automatic sequence of the entire panel and reviewing the images for artifacts. If any problems are found, the PLUT process just described can be performed for the tiles that were not properly aligned.

Figure 5:
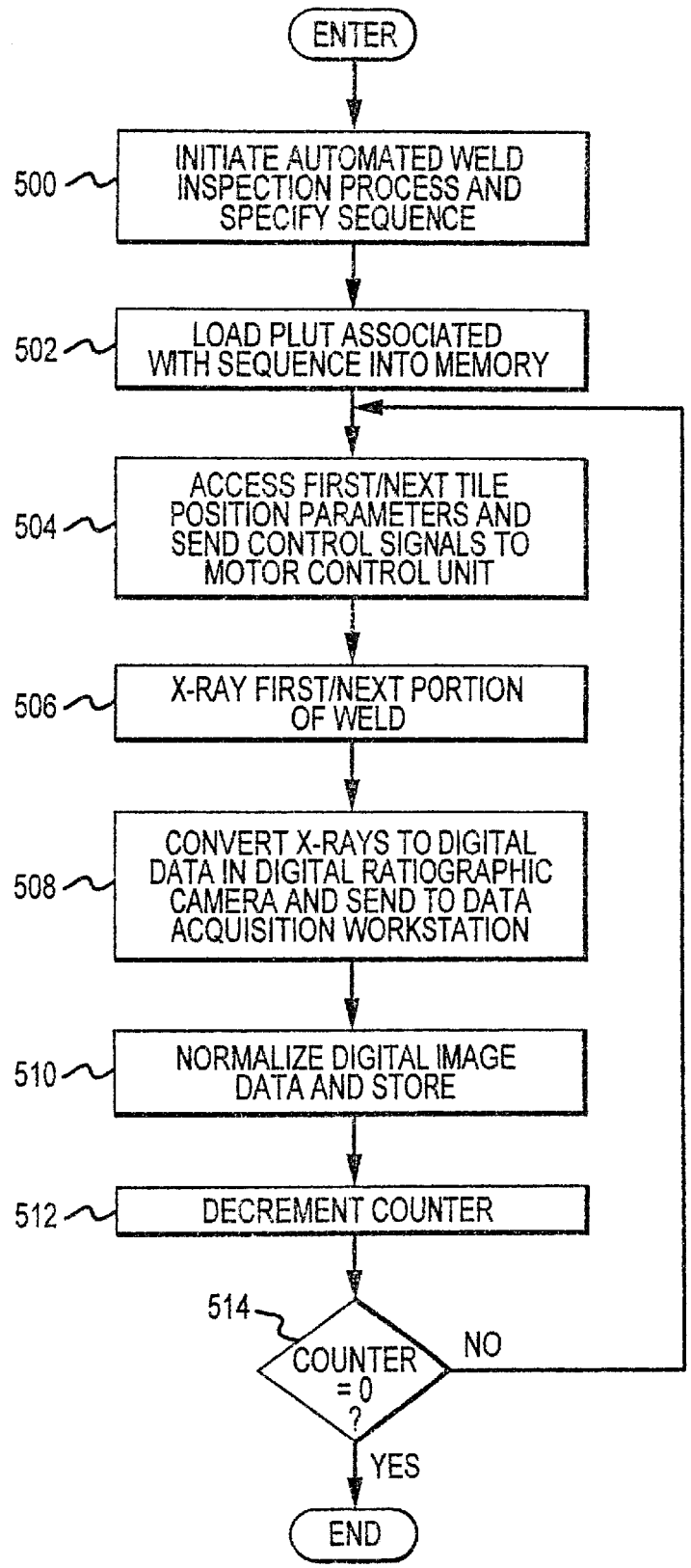
FIG. 5 shows a block diagram of generating tile images for weld inspection in the weld inspection system of the present invention.

FIG. 5 shows a block diagram of generating tile images for weld inspection in the weld inspection system of the present invention. An image normalization file from FIG. 3 and a PLUT from FIG. 4 for the vertical weld fixture 100 must be available in computer 212 (FIG. 2). Referring now to FIG. 5, in step 500 the automated weld inspection process is initiated within the imaging display and control software, specifying the image normalization file and the sequence to use for the type of welded barrel panels to be inspected. In step 502 the portion of the PLUT specified by the sequence selected in step 500 is loaded into memory in computer 212. In step 504 the parameters from the PLUT for the first tile position are accessed, and control signals are sent to motor control unit 130 to actuate all the parameters, including positioning camera carriage 112 and X-ray carriage 118 vertically at the first tile position, positioning digital radiographic camera 110 radially, positioning X-ray source 116 tangentially, etc. (FIG. 1).

In step 506 the first portion of weld 200 is X-rayed by X-ray source 116 for the exposure time specified in the parameters for the first tile position, with signals sent from computer 212 to control the opening and closing of the shutter on X-ray source 116. In step 508 the X-rays striking the fiber optic scintillator of digital radiographic camera 110 are converted to light, directed to the CCD chip, and read out by camera electronics unit 142 (FIG. 1) as a digital data set to interface 210 (FIG. 2) where it is formatted and sent on to computer 212 in data acquisition workstation 126. Step 510 normalizes the digital data set. The resulting tile image is automatically given a file name and stored on a hard drive in computer 212.

Step 512 decrements a counter for the number of tile positions that have been X-rayed. Step 514 then determines if the counter has reached zero. If the counter has not reached zero, then control returns to step 504 where steps 504 through 512 are repeated for the second tile position. Each iteration accesses the parameters for each tile position stored in the PLUT, sending control signals to motor control unit 130, X-raying the next portion of weld 200 (FIG. 2), and storing each tile image generated. When step 514 determines that the counter has reached zero, then the automated tile image generation process ends.

Figure 6:
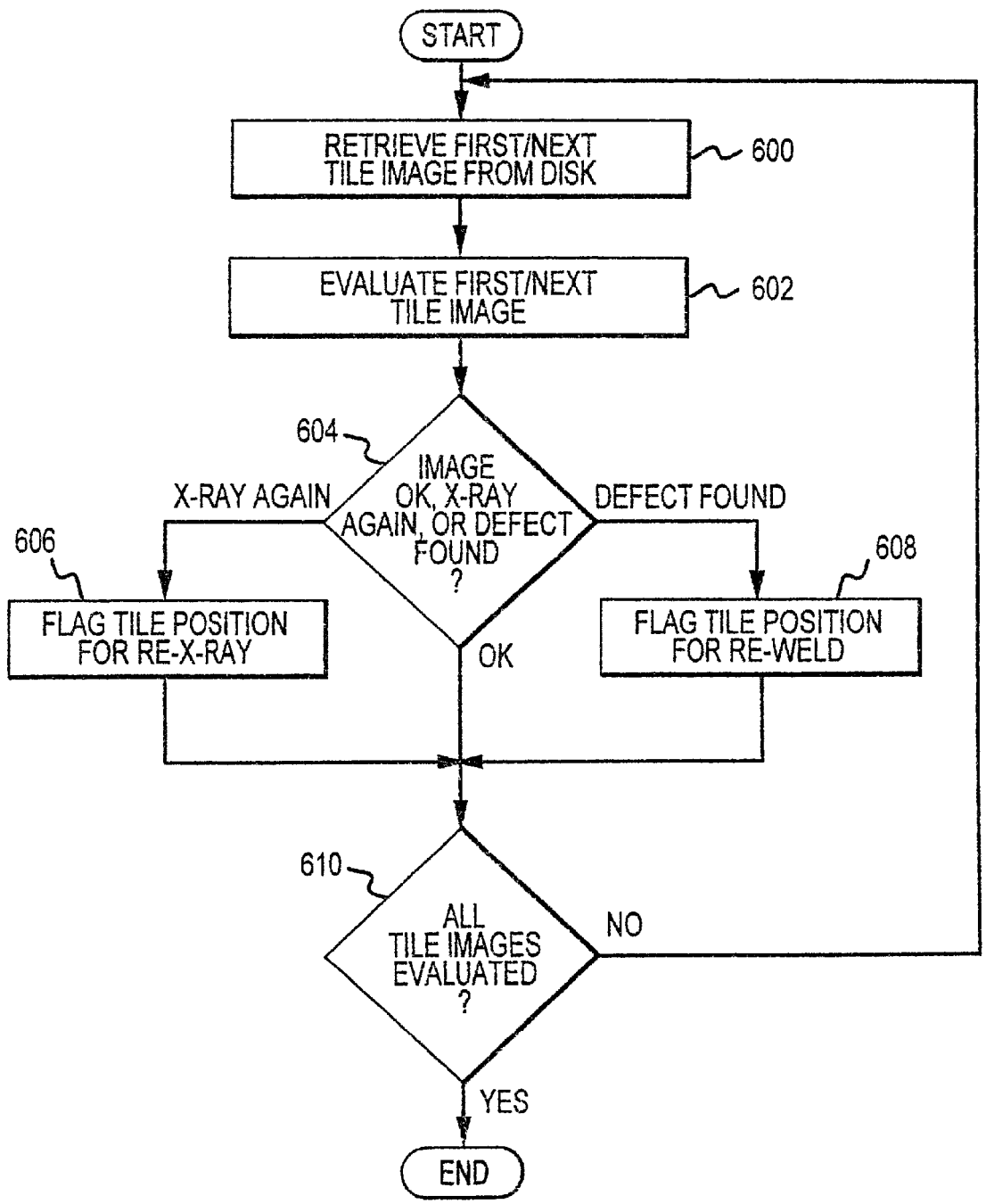
FIG. 6 shows a block diagram of reviewing tile images generated in FIG. 5 of the weld inspection system of the present invention.

FIG. 6 shows a block diagram of reviewing tile images generated in FIG. 5 of the weld inspection system of the present invention. Referring now to FIG. 6, reviewing tile images on image review workstation 192 (FIG. 1) can begin as soon as the first tile image is stored. When data acquisition workstation 126 is in the automated weld inspection mode, it cannot be used to do a detailed review of tile images. Image review workstation 192 allows detailed tile image review to be done at the same time tile images are being generated by data acquisition workstation 126. In step 600 the first tile image for the first tile position generated in FIG. 5 is retrieved from disk, and displayed on display devices 226 and 228 (FIG. 2). In step 602 the operator at image review workstation 192 can do a detailed evaluation of each tile image for any weld defects. Step 604 determines if input is received from the operator indicating that no defect was found, a defect was found, or if the portion of weld 200 (FIG. 2) represented by the tile image needs to be X-rayed again. If a clear defect is found, then in step 608 the tile position corresponding to the tile image is flagged for re-welding. Control then passes to step 610. If it is determined in step 604 that there is something suspicious about the tile image, or the quality of the weld image is not what it should be, then in step 606 the tile position corresponding to the tile image is flagged to be re-X-rayed. The operator may choose to alter any of the parameters for this tile position, such as the tangential source position or the radial camera position, to obtain a slightly different look at the portion of weld 200 in question. Control then passes to step 610.

If no clear defect is found in the tile image, and there is nothing suspicious about the tile image, control passes to step 610. Step 610 determines if all the tile images generated in FIG. 5 have been reviewed by the operator. If not, then control returns to step 600 where the next tile image is retrieved from disk for display on display devices 226 and 228. If all of the tile images generated in FIG. 5 have been reviewed, then the tile image review process ends.

Figure 7:
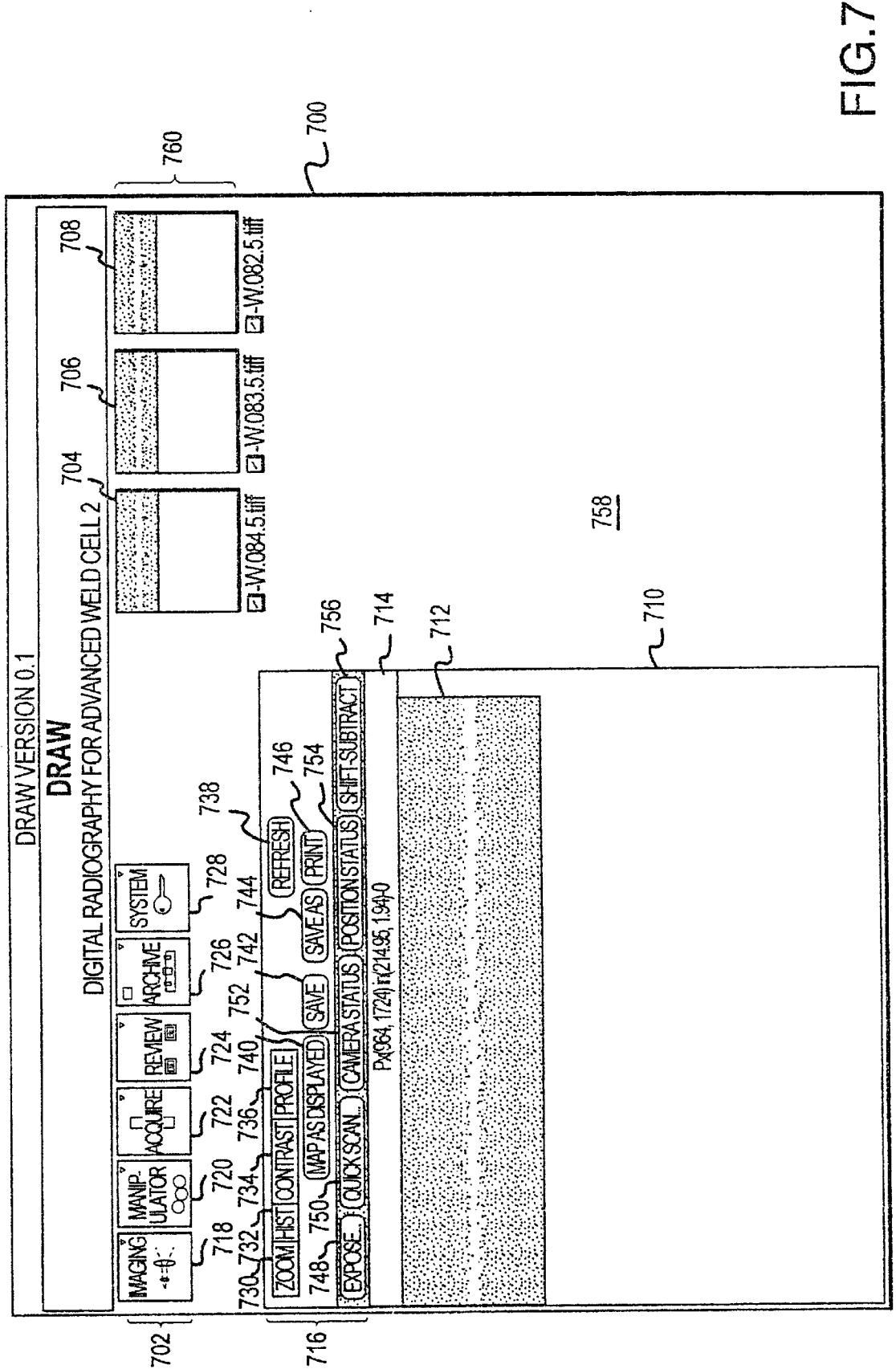
FIG. 7 shows a representation of the graphic user interface of the main screen of the imaging display and control software of the weld inspection system of the present invention.

FIG. 7 shows a representation of the graphic user interface of the main screen of the imaging display and control software of the weld inspection system of the present invention. Referring now to FIG. 7, main screen 700 may be displayed on either display device 216 in data acquisition workstation 126 or display device 228 in image review workstation 192 (FIG. 2). For discussion purposes of FIG. 7, it is assumed that main screen 700 is displayed on display device 216 in data acquisition workstation 126.

Icon row 702 is used to bring up menu windows for various operations. Clicking with mouse 220 on any of the icons in icon row 702 will display further menu options. Overview window control box 716 contains buttons for invoking various functions. Thumbnail tile images 704, 706, and 708 in thumbnail window row 760 indicate the last three tile images currently residing on the tile image stack. Overview tile image 712 displayed in overview image window 710, thumbnail tile image 704, and the full tile image that is displayed in a tile image window (not shown in FIG. 7) on display device 214 in data acquisition workstation 126 (FIG. 2), are all graphic representations of the same tile image data. Overview tile image 712 displayed in overview image window 710 is useful for orientation when zooming and contrast stretching the full tile image as displayed in display device 214.

Thumbnail tile images 704, 706, and 708 are displayed with the weld running horizontally on the screen. The left side of each tile image is down and the right side of each tile image is up in relation to the weld as held in vertical weld fixture 100 (FIG. 1). Thumbnail tile image 704 is the most recent addition to the tile image stack, and thumbnail tile image 708 is the oldest addition. Each new tile image read in from digital radiographic camera 110, or from external storage devices 222 or 234, is added in the position held by thumbnail tile image 704, bumping the existing tile images over one position, with the tile image that was in the position held by thumbnail tile image 708 being deleted from current tile image memory.

In overview image window 710 and in the tile image window in display device 214, boxes can be drawn by holding down the left mouse button starting at one apex and dragging the mouse to the opposite apex of the desired rectangle and releasing the mouse. Moving the mouse around in either tile image window displays the current coordinates of the mouse and the digital number at that coordinate in border 714 at the top of overview image window 710.

Imaging icon 718 is used to access all camera and tile image processing functions. The most commonly used items under imaging icon 718 can also be selected by clicking on buttons in overview window control box 716.

Manipulator icon 720 is used to prepare camera carriage 112 and X-ray carriage 118 for use. The primary functions are to initialize the four axes 240, 242, 244, and 246 so the computer knows where X-ray source 116 and digital radiographic camera 110 are at all times, and to move X-ray source 116 and digital radiographic camera 110 to the top and bottom park positions.

Acquire icon 722 controls most of the functions needed for obtaining barrel weld radiography data. The order in which the functions are performed follows the order of the items in the Acquire Menu shown by clicking with mouse 220 on acquire icon 722.

Review icon 724 is used to review a series of tile images while recording comments into a log file or to load a single saved tile image. Archive icon 726 is used to archive tile images from disk to a more permanent storage media and free up space on the disk. System icon 728 is used to log off the system and mount/dismount an optical disk. Clicking with mouse 220 on system icon 728 displays the System Menu. Selecting logoff from the System Menu brings up the logoff window for exiting the program.

When the cursor of mouse 220 is moved into overview image window 710, it converts to a colored cross-type cursor. The cursor location in the tile image and the pixel digital number at that location are shown in border 714. The cursor location and digital number are also shown in border 714 when the cursor is in the tile image window in display device 214.

Clicking on Zoom Button 730 turns the cursor into a red square when it is inside overview image window 710 (not shown in FIG. 7. The size of the square indicates the zoom to be applied to the tile image. Zooms of 1, 2, 4, and 8 are available.

Clicking on Histogram Button 732 will bring up a histogram window (not shown in FIG. 7) in quadrant 758. Moving the cursor in overview image window 710 or in the tile image window in display device 214 while the left mouse button is depressed will create a box around a region of interest. When the left mouse button is released, the statistics for the pixels within the box will be displayed below a plot of their histogram. The histogram is a plot of the number of pixels with a given X-ray brightness digital number (vertically) plotted against the X-ray brightness digital number (horizontally) Statistical parameters for the pixels contained in the region of interest are also displayed in the histogram -window. Such parameters include the minimum X-ray brightness digital number in any pixel, the maximum X-ray brightness digital number in any pixel, the mean X-ray brightness of all pixel values, the median X-ray brightness of pixel values, and the number of pixels included in the measurement. The location of the region of interest is given as coordinate pairs for the upper left apex and lower right apex, along with the width and height of the region of interest.

Clicking on Contrast Button 734 will bring up a contrast control window (not shown in FIG. 7) in quadrant 758. An Equalize Option presented in the contrast control window executes a special windowing technique called histogram equalization. This method allows the full range of brightness levels of the tile image to be visible at the same time. A Stretch Option windows the tile image based on the highest and lowest pixel values in the tile image. Both the Equalize and Stretch Options will apply to either All Pixels or Zoomed Region, depending upon which mode button is selected in the contrast control window.

The Window Sliders in the contrast control window controls the contrast and brightness of the tile image display. On the contrast slider, the numbers appearing at the end of the slider are the total range of pixel amplitudes seen in the last contrast adjustment. These numbers normally change every time a new box is drawn in the tile image, but they can be frozen by clicking the Fixed Limits box. The Brightness Slider is the pixel amplitude around which the contrast range is centered. Both Sliders can be easily adjusted by the operator with mouse 220.

Primarily four contrast mapping functions selected from historical use, which rapidly change the method of presenting the tile image, are also presented in the contrast control window under Mapping. The four options are Linear, Inverse Linear, Log, and Inverse Log. Both Inverse Mapping Options produce a tile image that, like radiographic film, displays lower X-ray intensity as white and higher X-ray intensity as black. The digital numbers on the Sliders are not changed by changes in contrast mode. These functions operate only on the tile image as it is displayed, and not on the original tile image data. These mapping functions are possible because the data is digital, in stark contrast to film techniques.

Clicking on Profile Button 736 will bring up an imaging profile window (not shown in FIG. 7) in quadrant 758. Profiles can be made of a single line of pixels or the average of up to 32 lines. Selecting the Horizontal or Vertical Type Buttons presented in imaging profile window, and then clicking on a location in overview image window 710 or in the tile image window in display device 214 gives a profile across the entire tile image in the indicated direction. Clicking the Line Button allows the operator to draw a line of any arbitrary length and direction by moving the mouse while the left mouse button is depressed. Profiles can be scaled by using the mouse to draw a box around a portion of the profile of interest. When the mouse button is released, that portion of the profile within the box will automatically be scaled to fill the profile window. Clicking on Reset Scale Button returns the profile to its original scale.

Boxes drawn in overview image window 710 or in the tile image window in display device 214 for contrast adjustment or histograms are not erased when a new location for a box is chosen. Clicking on Refresh Button 738 will erase all boxes currently being displayed.

Clicking on Map As Displayed Button 740 causes the tile image in overview image window 710 and the tile images in thumbnail window row 760 to be displayed with the same contrast adjustment as currently used for the tile image window in display device 214.

Save Button 742 allows the operator to save the full image data file of the leftmost tile image, thumbnail tile image 704, in a default directory location with an automatic file name that is self incrementing. Save As Button 744 allows the operator to save the leftmost tile image, thumbnail tile image 704, in an operator specified directory with an operator specified name.

Clicking on Print Button 746 brings up a print control window (not shown in FIG. 7) in quadrant 758. The print function allows the operator to generate a hard copy print of the tile image as shown in overview image window 710 including the current zoom, contrast adjustment, and any annotations. In addition, the tile image can be printed to a file as an eight bit image, using a tiff file format, that can later be read back in. These eight bit tiff files can also be read by many other imaging applications available in Unix, Mac, and PC computers.

Figure 8:
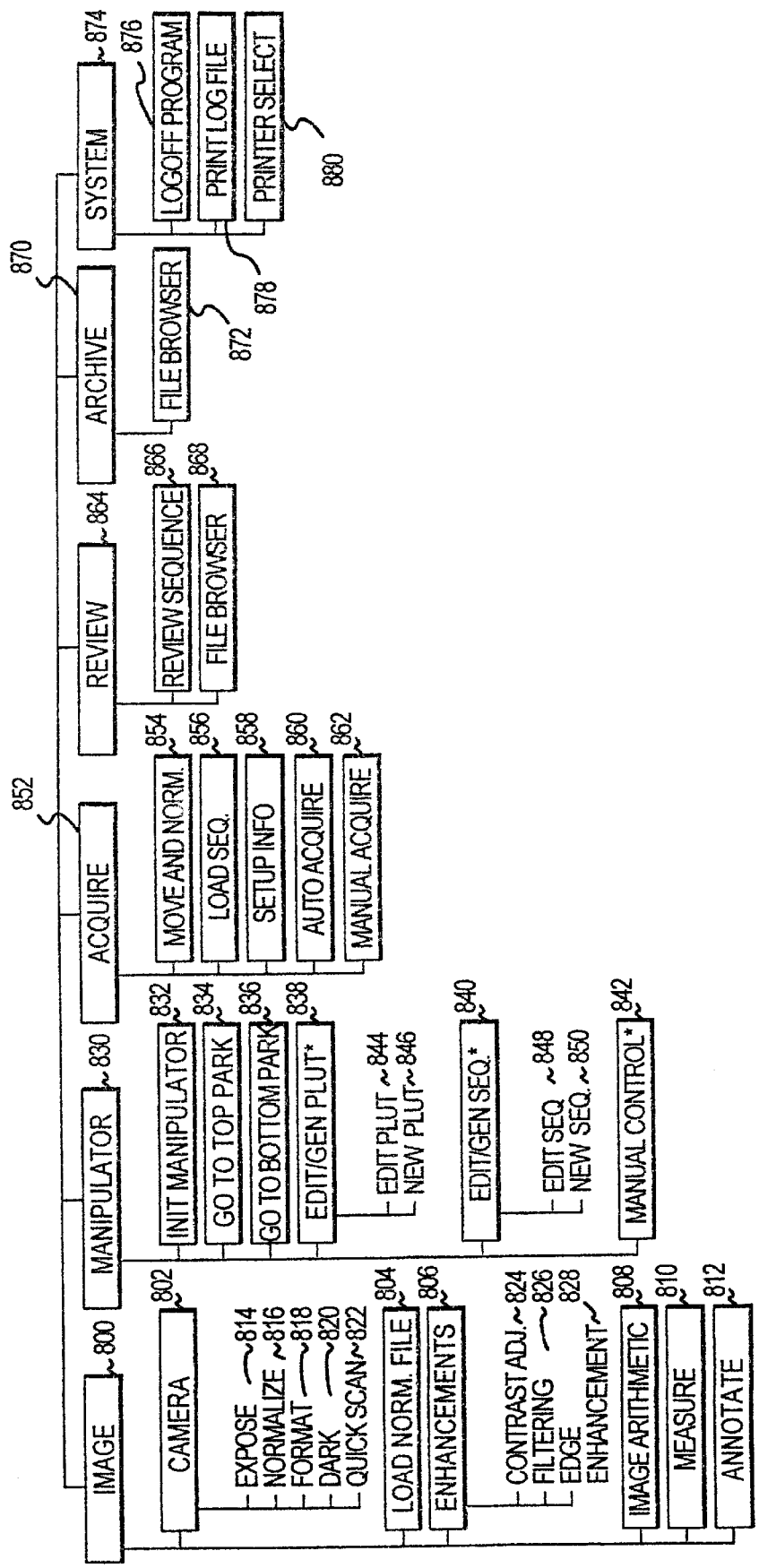
FIG. 8 shows the overall icon and menu layout of the imaging display and control software of the weld inspection system of the present invention.

Expose Button 748, Quick Scan Button 750, and Shift-Subtract Button 756 provide rapid short cuts when clicked on with mouse 220 to their associated functions, which are more fully described in FIG. 8.

Clicking on Camera Status Button 752 brings up a camera status window (not shown in FIG. 7) in quadrant 758. This window shows the current temperature of the CCD chip. This window does not update automatically. The current temperature can be read by closing and reopening the window, or by clicking on an Update Status Button presented in the window.

Clicking on Position Status Button 754 brings up a position status window (not shown in FIG. 7) in quadrant 758. This window shows the current location of digital radiographic camera 110 and X-ray source 116. This window does not update automatically. The latest position can be read by closing and reopening the window, or by clicking on an Update Status Button presented in the window.

FIG. 8 shows a block diagram of the overall icon and menu layout of the imaging display and control software of the weld inspection system of the present invention. Referring now to FIG. 8, image block 800 represents imaging icon 718 which is presented in main screen 700 (FIG. 7) as displayed on display device 216 in data acquisition workstation 126 (FIG. 2). When an operator selects imaging icon 718 with mouse 220 (FIG. 2) an Imaging Menu Window is displayed below imaging icon 718 containing various menu options which access an associated function. The menu options available in the Imaging Menu Window are: Camera Option 802, Load Normalization File Option 804, Enhancements Option 806, Image Arithmetic Option 808, Measure Option 810, and Annotate Option 812. Clicking with mouse 220 on a menu option will access the associated function, or bring up another menu window with a list of menu options to choose from.

When an operator selects Camera Option 802 with mouse 220, an Imaging/Camera Menu Window is displayed to the right of the Imaging Menu Window in main screen 700 and contains various submenu options which access an associated function. The submenu options available in the Imaging/Camera Menu Window are: Expose Option 814, Normalize Option 816, Format Option 818, Dark Option 820, Quick Scan Option 822, and Camera Status Option 824.

Selecting Expose Option 814 from the Imaging/Camera Menu Window with mouse 220 opens an expose window to the right of the Imaging/Camera Menu Window. This expose window may also be opened by clicking on Expose Button 748 in overview window control box 716 in main screen 700. The expose window allows an operator to enter the exposure time desired (in seconds). Next, either a No or Yes Option must be selected in response to the Perform Correction Option. Selecting No yields an un-normalized tile image which contains all of the fixed pattern noise in the camera system. Un-normalized tile images, however, are useful for establishing an exposure time to be used for a given inspection. Selecting Yes will automatically give a normalized tile image.

Clicking on the Expose and Display Option will start the camera exposure, correct the tile image if requested and display it as soon as the operations are completed. Clicking on the Expose Only Option starts the camera exposure and holds the tile image data in the camera memory when exposure and read out is completed. Computer 212 beeps when the exposure is completed. Clicking on the Display Option brings up the new tile image. Clicking on the Stop Option stops the action of displaying a tile image, but all other ongoing processes continue.

Selecting Normalize Option 816 from the Imaging/Camera Menu Window with mouse 220 opens a normalize window to the right of the Imaging/Camera Menu Window. This normalize window will typically be opened by clicking on acquire icon 722 in main screen 700 and then using the move and normalize menu selection. By obtaining the normalize window through the latter path, digital radiographic camera 110 and X-ray source 116 are automatically moved to the correct location for obtaining an image normalization set before the normalize window appears.

Selecting Format Option 818 from the Imaging/Camera Menu Window with mouse 220 opens a camera format window to the right of the Imaging/Camera Menu Window. The default values for the digital radiographic camera 110 format are kept in a text file. The camera format window enables adjustment of the digital radiographic camera 110 format. Once the format has been changed and the Apply Option has been clicked, all successive tile images acquired with digital radiographic camera 110 will have this new format. Once the digital radiographic camera 110 format has been modified, a new image normalization file must be obtained.

Selecting Dark Option 820 from the Imaging/Camera Menu Window with mouse 220 opens a dark window to the right of the Imaging/Camera Menu Window. This function, and its data input window, are similar to the Expose Option 814 except the image is acquired without X-rays. This function provides a tile image where the pixel amplitudes are the result of leakage currents and offsets. X-ray source 116 need not be turned off because the dark exposure will not open the X-ray shutter.

Selecting Quick Scan Option 822 from the Imaging/Camera Menu Window with mouse 220 opens a quick scan window to the right of the Imaging/Camera Menu Window. This function provides a continuously and rapidly updated tile image of a sample. Its primary use is to locate specific features of the sample in the field of view of digital radiographic camera 110. The initial exposure time is automatically set to 1/64th of that of the last exposure, but may be modified if desired. Clicking on an OK Option starts the operation. The tile image on display device 216 will update every few seconds with a tile image that provides higher noise and lower resolution, but rapid updates. The tile images displayed are uncorrected. The contrast settings update as the intensity in the tile image varies. Clicking on a Stop Option exits Quick Scan Option 822.

When an operator selects Load Normalization File Option 804 with mouse 220 a file browser window is displayed to the right of the Imaging Menu Window in main screen 700. With this option a previously acquired and saved image normalization file can be read in and re-used. The file browser window shows a list of files with the date, time, tile image size, and bin value at the time of creation encoded in the file names. The operator selects the file desired and it is loaded. The parameters used when the file was created are shown in a normalization parameters window that opens up. The bin value refers to the process where the charge stored in adjacent row and column pixels are added together to increase the sensitivity while reducing the resolution.

When an operator selects Enhancements Option 806 with mouse 220 an Enhancement Menu Window is displayed to the right of the Imaging Menu Window in main screen 700 and contains various submenu options which access an associated function. The submenu options available in the Enhancement Menu Window are: Contrast Adjustment Option 824, Filtering Option 826, and Edge Enhancement Option 828.

Selecting Contrast Adjustment Option 824 from the Enhancement Menu Window with mouse 220 brings up the same window as clicking on Contrast Button 734 in overview window control box 716, and is usually selected by that procedure.

Selecting Filtering Option 826 from the Enhancement Menu Window with mouse 220 brings up a filtering window which presents five different filtering options.

Selecting Edge Enhancement Option 828 from the Enhancement Menu Window with mouse 220 brings up an edge enhancement window which presents three different predetermined edge enhancement options including shift-subtract, which is usually selected by Shift-Subtract Button 756 in overview window control box 716.

When an operator selects Image Arithmetic Option 808 with mouse 220 an Image Arithmetic Menu Window is displayed to the right of the Imaging Menu Window in main screen 700. This option allows addition or subtraction of the first two tile images in the tile image stack, or the addition, subtraction, multiplication, or division of the first tile image by a constant. This is another benefit of utilizing digital data.

When an operator selects Measure Option 810 with mouse 220 a measure length window is displayed to the right of the Imaging Menu Window in main screen 700. This measure function provides the length of a line in pixels to size the defect. The line start and end point coordinates are also given.

When an operator selects Annotate Option 812 with mouse 220 an annotate window is displayed to the right of the Imaging Menu Window in main screen 700. Clicking on an Annotation Option in the annotate window starts the annotation process. All of the annotations except text are made by depressing the left mouse button and moving mouse 220. The available annotations are: a straight line, a line with an arrowhead at the end, a circle whose size is varied as the cursor is moved, a rectangle whose size is varied as the cursor is moved, text typed using keyboard 218, and an eraser function to delete annotations. All annotations may be erased by clicking on the Clear Option.

Manipulator block 830 represents manipulator icon 720 which is presented in main screen 700 (FIG. 7) as displayed on display device 216 in data acquisition workstation 126 (FIG. 2). When an operator selects manipulator icon 720 with mouse 220 a Manipulator Menu Window is displayed below manipulator icon 720 containing various menu options which access an associated function. The menu options available in the Manipulator Menu Window are: Initialize Manipulator Option 832, Go to Top Park Option 834, Go to Bottom Park Option 836, Edit/Generate PLUT Option 838, Edit/Generate Sequence Option 840, And Manual Control Option 842. Clicking with mouse 220 on a menu option will access the associated function, or bring up another menu window with a list of menu options to choose from.

When an operator selects Initialize Manipulator Option 832 with mouse 220 from the Manipulator Menu Window, a warning message window appears in quadrant 758 reminding the operator to verify that it is safe to move digital radiographic camera 110 and X-ray source 116. The operator must click on an OK or Cancel Option within the warning message window to proceed. The imaging display and control software then finds the initialize location along each of the axes 240, 242, 244, and 246. When completed, the tangential source position, the radial camera position, the vertical source position, and the vertical camera position will be at their respective known initialization positions. The motion has completed successfully when the "busy" mouse cursor is replaced by the normal mouse cursor and the message "Initialization Completed Successfully" appears in quadrant 758. If there is a problem with reaching the initialization position along any of the axes 240, 242, 244, and 246, an error message appears in quadrant 758.

When an operator selects Go to Top Park Option 834 with mouse 220 from the Manipulator Menu Window, a warning message window appears in quadrant 758 reminding the operator to verify that it is safe to move digital radiographic camera 110 and X-ray source 116. The operator must click on an OK or Cancel Option within the warning message window to proceed. Digital radiographic camera 110 and X-ray source 116 are then moved by the imaging display and control software to their respective top park positions on inside column 114 and outside column 120 (FIG. 1). Digital radiographic camera 110 and X-ray source 116 are moved to their respective top park positions whenever barrel panels 102 are to be placed on turntable 104 or routing of the weld is to be performed. Digital radiographic camera 110 is moved to its radial camera initialization position, and X-ray source 116 is moved to its tangential source initialization position by this command. The motion has completed successfully when the "busy" mouse cursor is replaced by the normal mouse cursor and the message "Top Park Completed Successfully" appears in quadrant 758. If there is a problem with reaching the initialization position along any of the axes 240, 242, 244, and 246, an error message appears in quadrant 758.

When an operator selects Go to Bottom Park Option 836 with mouse 220 from the Manipulator Menu Window, a warning message window appears in quadrant 758 reminding the operator to verify that it is safe to move digital radiographic camera 110 and X-ray source 116. The operator must click on an OK or Cancel Option within the warning message window to proceed. Digital radiographic camera 110 and X-ray source 116 are then moved by the imaging display and control software to their respective bottom park positions on inside column 114 and outside column 120. Digital radiographic camera 110 and X-ray source 116 are moved to their respective bottom park positions whenever welding is to be performed. Digital radiographic camera 110 is moved to its radial camera initialization position, and X-ray source 116 is moved to its tangential source initialization position by this command. The motion has completed successfully when the "busy" mouse cursor is replaced by the normal mouse cursor and the message "Bottom Park Completed Successfully" appears in quadrant 758. If there is a problem with reaching the initialization position along any of the axes 240, 242, 244, and 246, an error message appears in quadrant 758.

When an operator selects Edit/Generate PLUT Option 838 with mouse 220, an Edit/Generate PLUT Menu Window is displayed to the right of the Manipulator Menu Window in main screen 700 and contains various submenu options which access an associated function. The submenu options available in the Edit/Generate PLUT Menu Window are: Edit PLUT Option 844 and New PLUT Option 846.

Selecting New PLUT Option 846 from the Edit/Generate PLUT Menu Window with mouse 220 opens a generate PLUT window. A PLUT file is an ASCII file generated by the imaging display and control software that maintains a table of the locations of digital radiographic camera 110 and X-ray source 116 along each of the axes 240, 242, 244, and 246 for each tile image position along the length of weld 200. PLUT files are stored to disk The operator then enters data on each of the lines presented in the generate PLUT window. The operator specifies the vertical location for the bottom edge of the first tile image, the vertical location for the top edge of the last tile image, the vertical center to center tile image spacing, the radial camera location, and the tangent source location. The operator then selects Save to save the new PLUT or Cancel to quit. If Save is selected the new PLUT file is automatically named according to the current date and time and stored in the PLUT directory and overwrites the PLUT stored in memory. The adjust PLUT for alignment window then opens up and is used as was described in the detailed description of FIG. 4. Selecting edit PLUT option 844 from the Edit/Generate PLUT Menu Window with mouse 220 opens a browser window. After selecting a PLUT file, the author, description, date and setup parameters originally used to generate the selected PLUT are displayed. If the operator selects Cancel, no changes to the PLUT stored in memory are made. If the operator selects Accept, then the selected PLUT values become the current PLUT in memory. In addition, the Adjust PLUT for Alignment window is opened and is used as described in the Detailed Description of FIG. 4.

Sequence files are ASCII text files and can be edited and created by using a text editor. Sequences are one level of control higher than the PLUT tables. Each sequence makes use of a PLUT table. The first and last tile out of that PLUT table that are normally used for the sequence are selected. The number of tile images to step between tile images is also set. Sequence files are utilized as described below.

When an operator selects Edit/Generate Sequence Option 840 with mouse 220, an Edit/Generate Sequence Menu Window is displayed to the right of the Manipulator Menu Window in main screen 700 and contains various submenu options which access an associated function. The submenu options available in the Edit/Generate Sequence Menu Window are: Edit Sequence Option 848 and New Sequence Option 850.

Selecting New Sequence Option 850 from the Edit/Generate Sequence Menu Window with mouse 220 opens the generate/edit sequence window. After entering the parameters required for a new sequence, the operator must select Save to save the new sequence as a file or Cancel to quit. If Save is selected the new sequence is stored in a file in the sequence directory and overwrites the sequence stored in memory.

Selecting Edit Sequence Option 848 from the Edit/Generate Sequence Menu Window with mouse 220 opens a browser window. After selecting a sequence file to edit, a sequence information window is displayed which shows the existing parameters for the sequence. The operator must select Accept to edit the sequence file or Cancel to quit. If Accept is selected a generate/edit sequence window is displayed. After making any changes to the parameters, the operator must select Save to save the edited sequence file or Cancel to quit. If Save is selected the edited sequence file is stored in the sequence directory and overwrites the sequence stored in memory.

When an operator selects Manual Control Option 842 with mouse 220 from the Manipulator Menu Window, a manual control window is displayed in quadrant 758. From this window an operator can independently move digital radiographic camera 110 along axes 240 and 242, and X-ray source 116 along axes 244 and 246 by entering in the number of inches the operator desires either of them to move. Digital radiographic camera 110 can also be moved along axis 240 to the top park, initialization, and bottom park positions, and along axis 242 to the initialization position, by selecting that option. X-ray source 116 can also be moved along axis 244 to the top park, initialization, and bottom park positions, and along axis 246 to the initialization position, by selecting that option. After a move command is entered, while the move is in process a "Moving" message appears at the top of the window. The current move must complete before making the next move.

Acquire block 852 represents acquire icon 722 which is presented in main screen 700 (FIG. 7) as displayed on display device 216 in data acquisition workstation 126 (FIG. 2). Acquire icon 722 is only available after Initialize Manipulator Option 832 has been performed. That is, the functions accessed through Acquire icon 722 are only active once the manipulator position has been initialized because all functions require that the computer know the location of the initialization switch position in order to operate correctly.

When an operator selects acquire icon 722 with mouse 220, an Acquire Menu Window is displayed below manipulator icon 720 containing various menu options which access an associated function. The menu options available in the Acquire Menu Window are: move and Normalize Option 854, Load Sequence Option 856, Setup Information Option 858, Auto Acquire Option 860, and Manual Acquire Option 862. Clicking with mouse 220 on a menu option will access the associated function, or bring up another menu window with a list of menu options to choose from.

When an operator selects Move And Normalize Option 854 with mouse 220 from the Acquire Menu Window, a prompt appears on display device 216 prompting the operator to ensure that there are no obstructions in the path of either digital radiographic camera 110 or X-ray source 116, and to turn on X-ray source 116 to the expected kV and mA settings. After digital radiographic camera 110 and X-ray source 116 have been moved to the location for obtaining an image normalization set, a normalize window is opened. The operator then follows the instructions in the normalize window for obtaining an image normalization file.

A default sequence is read when the imaging display and control software starts. an operator may load a new sequence by selecting the Load Sequence Option 856 with mouse 220 from the Acquire Menu Window. By loading a new sequence, the default sequence is superseded. After selecting Load Sequence Option 856, a file browser appears showing the available sequence files. After selecting a desired sequence file from the list, the sequence information window is displayed which shows the existing parameters for the sequence selected. The operator may select an Accept or Cancel Option. If the Cancel Option is selected, no change is made to the currently loaded sequence. If the Accept Option is selected, the new sequence information is stored in the parameter settings until a new sequence file is selected. Once the Accept Option has been selected, the operator is automatically taken to the function described in the Setup Information Option 858 described below.

When an operator selects Setup Information Option 858 with mouse 220 from the Acquire Menu Window, a setup information window appears in quadrant 758. The information stored in a sequence file can be applied to all barrel welds of a particular type. The setup information window allows an operator to enter specific information about the particular barrel panels 102 to be inspected. In addition, the file names for tile images and log file storage are automatically generated in this window. Setup Information Option 858 is the gatekeeper to the Auto Acquire Option 860 and the Manual Acquire Option 862 discussed below.

When an operator selects Auto Acquire Option 860 with mouse 220 from the Acquire Menu Window, an acquisition status window appears in quadrant 758. A message bar within the acquisition status window indicates the status of the automated tile image acquisition process, such as "Moving", "Exposing", "Saving", or "Idle". A image normalization file must be present, and if not, the automatic tile image acquisition process will not proceed.

When an operator selects Manual Acquire Option 862 with mouse 220 from the Acquire Menu Window, the acquisition status window described above and a manual acquisition control window appear in quadrant 758. Three mode buttons, Manual, Expose-Move, and Move-Expose, which are mutually exclusive, are presented in the manual acquisition control window. The default mode is Manual. Auto Save Buttons On and Off determine whether the tile image is automatically saved using the default filename. The default is the ON Button. In the Manual mode, two arrows buttons for Next or Previous tile, or a Go To Tile # Option, are used to move digital radiographic camera 110 and X-ray source 116. A separate Expose Button must then be clicked to take a tile image. When the mode is Move-Expose or Expose-Move, the separate Expose Button is disabled. If an image normalization file is present, it is always applied when the separate Expose Button is selected. If there is no image normalization file present, the operator is warned that no image normalization file has been acquired, but the operator is allowed to proceed by overriding the warning.

Review block 864 represents review icon 724 which is presented in main screen 700 (FIG. 7) as displayed on display device 216 in data acquisition workstation 126 (FIG. 2). When an operator selects review icon 724 with mouse 220, a Review Menu Window is displayed below review icon 724. containing various menu options which access an associated function. The menu options available in the Review Menu Window are: Review Sequence Option 866 and File Browser Option 868. Clicking with mouse 220 on a menu option will access the associated function, or bring up another menu window with a list of menu options to choose from.

When an operator selects Review Sequence Option 866 with mouse 220 from the Review Menu Window, a review setup window appears allowing the operator to select which barrel weld sequence to review. After selecting the barrel weld sequence, a review record window appears to assist in moving through the tile images in the selected sequence, and to record inspection comments into a log file. Selecting File Browser Option 868 allows an operator to select a single tile image, but does not record comments to a log file.

Archive block 870 represents archive icon 726 which is presented in main screen 700 (FIG. 7) as displayed on display device 216 in data acquisition workstation 126 (FIG. 2). When an operator selects archive icon 726 with mouse 220 an Archive Menu Window is displayed below review icon 724. Selecting File Browser Option 872 allows the operator to select directories to archive from the hard drive. Once the directories to archive are selected, the operator chooses the archive device. Data is copied form the disk to the selected storage media. The archival storage device may be tape, optical disk, writable CDROM, DVD or similar media. Once the directories are copied and verified, the operator chooses whether to delete the original data from hard disk.

System block 874 represents system icon 728 which is presented in main screen 700 (FIG. 7) as displayed on display device 216 in data acquisition workstation 126 (FIG. 2). When an operator selects system icon 728 with mouse 220 a System Menu Window is displayed below system icon 728 containing various menu options which access an associated function. The menu options available in the System Menu Window are: Logoff Program Option 876, Print Log File Option 878, and Printer Select Option 880. Clicking with mouse 220 on a menu option will access the associated function, or bring up another menu window with a list of menu options to choose from.

When an operator selects Logoff Program Option 876 with mouse 220 from the System Menu Window, a logoff window is displayed in quadrant 758. Clicking on the Yes Button will exit the imaging display and control software.

When an operator selects Print Log File Option 878 with mouse 220 from the System Menu Window, a print log file window is displayed in quadrant 758. A file browser displays the available files to print. Clicking on the Print Data Acquisition Button will print the data acquisition file selected to the default printer. Clicking on the Print Tile Image Review Log Button will print the tile image review log file selected to the default printer.

When an operator selects Printer Select Option 880 with mouse 220 from the System Menu Window, a printer selection window is displayed in quadrant 758. Printers 236 usually include a laser printer and a dye sublimation printer. All log file printing is sent to the laser printer. Tile images may be printed to either printer.

Having described a presently preferred embodiment of the present invention, it will be understood by those skilled in the art that many changes in construction and circuitry and widely differing embodiments and applications of the invention will suggest themselves without departing from the scope of the present invention, as defined in the claims. The idea of immediate digital radiography following welding will work with more than just vertical welding. One would simply modify the mechanical arrangement to deal with circumferential, horizontal, or other welding configurations. The disclosures and the description herein are intended to be illustrative and are not in any sense limiting of the invention, defined in scope by the following claims.

What is claimed is:

1. A method for inspecting a weld comprising the steps of:
    (a) positioning said weld between an X-ray source in a first source position and a digital radiographic camera in a first camera position, wherein said X-ray source and said digital radiographic camera are aligned relative to each other at said first source position and said first camera position to inspect said weld;
    (b) transmitting X-rays from said X-ray source through a first portion of said weld;
    (c) receiving said transmitted X-rays through said first portion of said weld in said digital radiographic camera;
    (d) converting said transmitted X-rays through said first portion of said weld within said digital radiographic camera into a first digital data set of said first portion of said weld; and
    (e) transmitting said first digital data set of said first portion of said weld from said digital radiographic camera to a first processor, wherein said first digital data set of said first portion of said weld is convertible to a displayable image.

2. A method for inspecting a weld according to claim 1 further comprising the steps of:
    (f) processing said first digital data set of said first portion of said weld with said first processor to generate a first tile image of said first portion of said weld; and
    (g) displaying said first tile image of said first portion of said weld on at least one display device.

3. A method for inspecting a weld according to claim 2 further comprising the steps of:
    (h) storing said first tile image of said first portion of said weld in a storage device;
    (i) transferring said first tile image of said first portion of said weld to a second processor; and
    (j) displaying said first tile image on at least one display device connected to said second processor.

4. A method for inspecting a weld according to claim 3 further comprising the steps of:
    (k) positioning said digital radiographic camera in a second camera position;
    (l) positioning said X-ray source in a second source position, wherein said X-ray source in said second source position and said digital radiographic camera in said second camera position are aligned relative to each other at said second source position and said second camera position to inspect said weld; and
    (m) repeating steps (b) through (j) for a second portion of said weld, yielding a second tile image of said second portion of said weld.

5. A method for inspecting a weld according to claim 4 further comprising the steps of:
    (n) repeating steps (k) through (m) for a plurality of next camera positions and a plurality of next source positions, wherein said X-ray source in said plurality of next source positions and said digital radiographic camera in said plurality of said next camera positions are each aligned relative to each other to inspect a remaining plurality of portions of said weld, yielding a plurality of next tile images of said remaining plurality of portions of said weld.

6. A method for inspecting a weld according to claim 1 wherein step (a) further comprises positioning said weld within a vertical weld fixture, wherein said weld is a fusion weld joining a first barrel panel and a second barrel panel.

7. A method for inspecting a weld according to claim 2 wherein said method for inspecting a weld further comprises the step (a0) performed before step (a):
    (a0) generating an image normalization file.

8. A method for inspecting a weld according to claim 7 wherein step (a0) further comprises the steps (a0a) through (a0l):
    (a0a) placing a material sample of a first material between said X-ray source and said digital radiographic camera, wherein said weld joins a first barrel panel made of said first material to a second barrel panel made of said first material;
    (a0b) aligning said X-ray source and said digital radiographic camera relative to each other to generate a normalization image set of said material sample;
    (a0c) transmitting X-rays from said X-ray source through said material sample;
    (a0d) receiving said transmitted X-rays through said material sample in said digital radiographic camera;
    (a0e) converting said transmitted X-rays within said digital radiographic camera into a normalization image set of said material sample;
    (a0f) transmitting said normalization image set of said material sample from said digital radiographic camera to said first processor;
    (a0g) stopping the transmission of said X-rays;
    (a0h) clearing said normalization image set from said digital radiographic camera;
    (a0i) building up charges within said digital radiographic camera;
    (a0j) converting said built up charges within said digital radiographic camera into a dark image set;
    (a0k) transmitting said dark image set from said digital radiographic camera to said first processor; and
    (a0l) combining said normalization image set and said dark image set to form said image normalization file.

9. A method for inspecting a weld according to claim 7 wherein step (f) comprises the step (f1):
    (f1) normalizing said first digital data set of said first portion of said weld with said image normalization file to generate said first tile image of said first portion of said weld.

10. A method for inspecting a weld according to claim 1 wherein step (a) comprises the following steps (a1) and (a2);
    (a1) positioning said digital radiographic camera in said first camera position with said first processor, wherein said first processor controls a first drive motor that moves a camera carriage, which houses said digital radiographic camera, along a first axis, wherein said first axis is parallel to and aligned with a longitudinal axis of said weld; and
    (a2) positioning said X-ray source in said first source position with said first processor, wherein said first processor controls a second drive motor that moves an X-ray carriage, which houses said X-ray source, along a second axis, wherein said second axis is parallel to and aligned with said longitudinal axis of said weld.

11. A method for inspecting a weld according to claim 10 wherein step (a1) comprises said first processor accessing a position look up table and transmitting a first camera carriage position value to a first encoder connected to said first drive motor to verify the positioning of said digital radiographic camera in said first camera position, and step (a2) comprises said first processor accessing said position look up table and transmitting a first X-ray carriage position value to a second encoder connected to said second drive motor to verify the positioning of said X-ray source in said first source position.

12. A method for inspecting a weld according to claim 10 wherein step (a1) comprises the step (a1a), and step (a2) comprises the step (a2a):

(a1a) positioning said digital radiographic camera in said first camera position with said first processor, wherein said first processor controls a third drive motor which moves said digital radiographic camera along a camera sub-slide within said camera carriage, wherein said camera sub-slide lies along a third axis which is perpendicular to said first axis and said longitudinal axis, and passes through said first axis and said longitudinal axis;

(a2a) positioning said X-ray source in said first source position with said first processor, wherein said first processor controls a fourth drive motor which moves said X-ray source along an X-ray sub-slide within said X-ray carriage, wherein said X-ray sub-slide lies along a fourth axis perpendicular to said second axis and perpendicular to said third axis.

13. A method for inspecting a weld according to claim 12 wherein step (a1a) comprises said first processor accessing a position look up table and transmitting a first camera sub-slide position value to said third drive motor to control the positioning of said digital radiographic camera along said camera sub-slide within said camera carriage, and step (a2a) comprises said first processor accessing said position look up table and transmitting a first X-ray sub-slide position value to said fourth drive motor to control the positioning of said X-ray source along said X-ray sub-slide within said X-ray carriage.

14. A method for inspecting a weld according to claim 13 wherein step (b) comprises the steps (b1) and (b2):

(b1) opening a shutter on a shielded housing surrounding said X-ray source for a predetermined period of time to allow said transmitted X-rays to escape said shielded housing and pass through said first portion of said weld, wherein said opening of said shutter is controlled by said first processor, and further wherein said predetermined period of time is accessed by said first processor from said position look up table; and (b2) closing said shutter after said predetermined period of time has passed, wherein said closing of said shutter is controlled by said first processor.

15. A method for inspecting a weld according to claim 1 wherein step (b) further comprises transmitting said X-rays through a collimator before said X-rays reach said first portion of said weld.

16. An apparatus for inspecting a weld, said apparatus comprising:

a first column having a camera carriage mounted thereon for movement there along;

a second column having an X-ray carriage mounted thereon for movement there along;

a base platform, wherein said first and second columns are secured thereon;

an X-ray source, mounted on said X-ray carriage, for transmitting X-rays through at least one portion of said weld;

a digital radiographic camera mounted on said camera carriage, wherein said at least one portion of said weld is positioned between said first and second columns such that said X-ray source on said X-ray carriage and said digital is radiographic camera on said camera carriage are aligned relative to each other to inspect said at least one portion of said weld, and further wherein said digital radiographic camera receives said transmitted X-rays through said at least one portion of said weld and generates at least one digital data set of said at least one portion of said weld, wherein said at least one digital data set is convertible to a displayable image.

17. An apparatus for inspecting a weld according to claim 16 further comprising:

a first processor for processing at least one digital data set of said at least one portion of said weld received from said digital radiographic camera to generate at least one tile image of said at least one portion of said weld; and at least one display device for displaying said at least one tile image of said at least one portion of said weld.

18. An apparatus for inspecting a weld according to claim 17 further comprising:

a first drive motor, controlled by said first processor, for moving said camera carriage along said first column along a first axis, wherein said first axis is parallel to and aligned with a longitudinal axis of said weld; and a second drive motor, controlled by said first processor, for moving said X-ray carriage along said second column along a second axis, wherein said second axis is parallel to and aligned with said longitudinal axis of said weld.

19. An apparatus for inspecting a weld according to claim 18 further comprising:

a position look up table within said first processor;

a first encoder connected to said first drive motor, wherein said first processor accesses said position look up table and transmits at least one first column position value to said first encoder to verify the positioning of said camera carriage along said first column; and a second encoder connected to said second drive motor, wherein said first processor accesses said position look up table and transmits at least one second column position value to said second encoder to verify the positioning of said X-ray carriage along said second column.

20. An apparatus for inspecting a weld according to claim 19 further comprising:

a shutter on a shielded housing surrounding said X-ray source controlled by said first processor, wherein said shutter is opened for at least one predetermined period of time to allow said transmitted X-rays to escape said shielded housing and through said at least one portion of said weld, and said shutter is closed by said first processor after said at least one predetermined period of time has passed, and further wherein said at least one predetermined period of time is accessed by said first processor from said position look up table.

21. An apparatus for inspecting a weld according to claim 18 further comprising:

a third drive motor controlled by said first processor for moving said digital radiographic camera along a camera sub-slide within said camera carriage, wherein said camera sub-slide lies along a third axis which is perpendicular to said first axis and said longitudinal axis, and passes through said first axis and said longitudinal axis; and a fourth drive motor controlled by said first processor for moving said X-ray source along an X-ray sub-slide within said X-ray carriage, wherein said X-ray sub-slide lies along a fourth axis perpendicular to said second axis and perpendicular to said third axis.

22. An apparatus for inspecting a weld according to claim 21 further comprising:

a position look up table within said first processor, wherein said first processor accesses said position look up table and transmits at least one camera sub-slide position value to said third drive motor to control the positioning of said digital radiographic camera along said camera sub-slide within said camera carriage, and transmits at least one X-ray sub-slide position value to said fourth drive motor to control the positioning of said X-ray source along said X-ray sub-slide within said X-ray carriage.

23. An apparatus for inspecting a weld according to claim 16 further comprising:

a second processor connected to said first processor, wherein said at least one tile image of said at least one portion of said weld is transferred from said first processor to said second processor; and at least one display device connected to said second processor for displaying said at least one tile image of said at least one portion of said weld.

24. An apparatus for inspecting a weld according to claim 16 further comprising:

a collimator attached to said X-ray source to limit said transmitted X-rays to a field of view of said digital radiographic camera.

* * * * *